US012715844B2

(12) United States Patent
Zhao et al.

(10) Patent No.: US 12,715,844 B2
(45) Date of Patent: Aug. 25, 2026

(54) COMPOUND, PREPARATION METHOD THEREFOR, COMPOSITION, KIT AND USE THEREOF

(71) Applicant: SIGNDO BIOTECHNOLOGY (SUZHOU) CO., LTD, Jiangsu (CN)

(72) Inventors: Jing Zhao, Jiangsu (CN); Lirong Yang, Jiangsu (CN)

(73) Assignee: SIGNDO BIOTECHNOLOGY (SUZHOU) CO., LTD, Jiangsu (CN)

( * ) Notice: Subject to any disclaimer, the term of this patent is extended or adjusted under 35 U.S.C. 154(b) by 0 days.

(21) Appl. No.: 19/274,714

(22) Filed: Jul. 21, 2025

(65) Prior Publication Data

US 2025/0346559 A1 Nov. 13, 2025

Related U.S. Application Data

(63) Continuation-in-part of application No. PCT/CN2024/085548, filed on Apr. 2, 2024.

(30) Foreign Application Priority Data

May 10, 2023 (CN) ......................... 202310522371.5

(51) Int. Cl.

*C07D 209/12* (2006.01)
*A61K 49/00* (2006.01)
*G01N 33/57555* (2026.01)
*G01N 33/58* (2006.01)

(52) U.S. Cl.

CPC ........ *C07D 209/12* (2013.01); *A61K 49/0021* (2013.01); *G01N 33/57555* (2026.01); *G01N 33/582* (2013.01)

(58) Field of Classification Search

CPC ................ C07D 209/12; C07D 209/02; A61K 49/0021; A61K 49/0052; A61K 49/0032; G01N 33/57434; G01N 33/582; G01N 33/533; G01N 21/6486; C09K 2211/1007; C09K 2211/1029; C09K 11/06

See application file for complete search history.

(56) References Cited

U.S. PATENT DOCUMENTS

2014/0271476 A1 9/2014 Kularatne et al.
2017/0065729 A1 3/2017 Kularatne et al.
2018/0099934 A1 4/2018 Kularatne et al.
2019/0151480 A1 5/2019 Kularatne et al.
2021/0347766 A1 11/2021 Kularatne et al.

FOREIGN PATENT DOCUMENTS

CN 103143013 A 6/2013
CN 112961173 A 6/2021
CN 113717089 A 11/2021
CN 116554274 A 8/2023

OTHER PUBLICATIONS

Jul. 12, 2024 International Search Report issued in International Patent Application No. PCT/CN2024/085548.
Jul. 12, 2024 Written Opinion of the International Searching Authority issued in International Patent Application No. PCT/CN2024/085548.
May 30, 2024 First Office Action of a corresponding Chinese Patent Application No. 202410495605.6.
Jun. 20, 2024 Second Office Action of a corresponding Chinese Patent Application No. 202410495605.6.
May 30, 2024 First Search Report of a corresponding Chinese Patent Application No. 202410495605.6.
Extended European Search Report Application No. /Patent No. 24802655.1 issued on Apr. 2, 2026.
Chen, Y. et al.: "A low molecular weight PSMA-based fluorescent imaging agent for cancer", Biochemical and Biophysical Research Communications Elsevier, Amsterdam NL, vol. 390, No. 3, Dec. 18, 2009 (Dec. 18, 2009), pp. 624-629, XP026770595,ISSN: 0006-291X, DOI: 10.1016/J.BBRC.2009.10.017.
Stibbe Judith A. et al.: "Detection of Prostate Cancer Metastases During Pelvic Lymph Node Dissection with the PSMA-Targeted Fluorescent Agent OTL78: A Phase II Study", Molecular Imaging & Biology Elsevier, Boston, vol. 27, No. 6, Oct. 9, 2025 (Oct. 9, 2025), pp. 976-983, XP038567048, ISSN: 1536-1632, DOI: 10.1007/S11307-025-02052-X.

*Primary Examiner* — Robert S Cabral

(74) *Attorney, Agent, or Firm* — Houston Beshining Law Office PLLC; Liangang Ye

(57) ABSTRACT

Provided in the present invention are a compound, a preparation method therefor, a composition, a kit, and the use thereof. The compound has a condensed structural formula as follows: wherein the cation M is selected from alkali metal cations, R is a C2-C5 alkyl, and n is an integer in the range of 2-5. The compound and an application product thereof have a good recognition ability and a good targeting performance for a PSMA receptor, can be widely applied to a plurality of scenarios such as flow cytometric analysis and in-vivo imaging in practical applications, and has the advantages of fast signal response speed, high resolution, good safety, excellent metabolic ability, etc.

19 Claims, 9 Drawing Sheets

100nmol/mouse
50nmol/mouse
25nmol/mouse

COMPOUND, PREPARATION METHOD THEREFOR, COMPOSITION, KIT AND USE THEREOF

CROSS-REFERENCE TO RELATED APPLICATIONS

This application is a continuation-in-part application of PCT/CN2024/085548, filed on Apr. 2, 2024, which claims the right of the priority of Chinese patent application filed with China National Intellectual Property Administration on May 10, 2023, with the application number 202310522371.5 and the title "COMPOUND, PREPARATION METHOD THEREFOR, COMPOSITION, KIT AND USE THEREOF". The contents of the application are incorporated herein by reference in their entireties.

TECHNICAL FIELD

The present disclosure belongs to the field of bioassay technology, specifically relates to a compound, a preparation method therefor, a composition, a kit, and a use thereof.

BACKGROUND

Prostate cancer (PCa) is one of the most common tumors that threaten men's health. In recent years, the incidence of prostate cancer in China has risen significantly, and now it has become the fastest-growing type among all malignant tumors. Due to the lack of sensitive imaging agents for the diagnosis and efficacy monitoring of prostate cancer, selecting an appropriate treatment plan remains a significant clinical challenge.

Accurate detection of prostate cancer in its early stages is crucial to patient treatment outcomes and survival. Prostate cancer is often difficult to be detected early due to its relatively slow progression. The combination of prostate-specific antigen (PSA), magnetic resonance imaging, and puncture biopsy can effectively diagnose PCa. However, there is currently a lack of functional imaging devices with high sensitivity and specificity that can define its biological behavior. Over the past decade, PET/CT has made significant advancements. By integrating PET—nuclear medicine molecular imaging with high sensitivity and specificity—and CT's fine anatomical imaging, PET/CT has demonstrated immense potential in various aspects such as preoperative diagnosis, staging, and treatment decision-making for primary prostate cancer. In treatment, radical prostatectomy is one of the most effective methods for treating localized and locally advanced prostate cancer. The determination of the range of resection margin by surgeons primarily relies on preoperative imaging examinations, intraoperative visual inspection and exploration, as well as the surgeon's own experience. Excessive surgical resection range can damage normal tissues and affect normal functions such as urinary control, while insufficient resection range can lead to positive resection margins, causing patients to be prone to recurrence. Therefore, how to preserve normal tissues and functions as much as possible during surgery while thoroughly resecting areas invaded by prostate cancer is a common challenge that clinicians frequently faced and needed to address.

Targeted fluorescence intraoperative navigation technology is the remedy to this problem. In the field of prostate cancer, there exists a highly specific molecular marker for prostate cancer—prostate-specific membrane antigen (PSMA). PSMA is overexpressed in 90% of prostate cancers, while only a small amount is expressed in normal tissues such as lacrimal glands, salivary glands, and renal proximal tubules. The expression level of PSMA in prostate cancer is highly correlated with tumor aggressiveness and malignancy. Prostate-specific membrane antigen (PSMA), a multifunctional type II transmembrane protein composed of 750 amino acid residues, is localized on the membrane of prostate cells. PSMA has high prostate tissue specificity, with a sensitivity and specificity of 65.9% and 94.5% in distinguishing prostate cancer from other types of malignant tumors, respectively. Therefore, PSMA remains a highly sensitive and specific antigen on prostate cancer cells. PSMA is superior to PSA in distinguishing benign from malignant prostate tissues, with its expression intensity increasing in advanced clinical stages and exhibiting a positive correlation with tumor malignancy. Therefore, PSMA is a more specific tumor marker for prostate cancer compared to PSA and can be used as an important indicator for prognostic evaluation of prostate cancer. Therefore, PSMA has become an ideal biomarker for precise localization imaging and intraoperative navigation of prostate cancer lesions. Near-infrared fluorescence surgical navigation technology targeting PSMA mainly utilizes the advantages of near-infrared dyes, such as long wavelength, strong tissue penetration, and little scattering. It enables the illumination of lesions during surgery, allowing surgeons to clearly visualize the extent of the lesions, thereby performing a more complete and effective resection. Therefore, near-infrared fluorescence surgical navigation targeting PSMA will be a highly promising surgical approach for the treatment of prostate cancer. Furthermore, the optical-nuclear medicine dual-modality molecular imaging probe can integrate the advantages of both imaging modalities, with high sensitivity and high precision to identify and locate diseased tissues preoperatively through the nuclear medicine modality, and to precisely mark the location of lesions with fluorescence intraoperatively to guide surgical resection.

The radionuclide diagnostic and surgical navigation drugs targeting PSMA currently used in clinical trials are all based on glutamate-urea as the basic skeleton. These probes have good targeting and affinity for PSMA, but there are problems of severe radionuclide retention in the bladder and high radionuclide background in the kidneys. The large amount of radionuclide retention in the bladder seriously affects the accuracy of early diagnosis of prostate cancer, while the high radionuclide background in both kidneys has certain toxic side effects on the kidneys. Therefore, it is imperative to develop PSMA molecular imaging probes with high specificity and low renal excretion by modifying the drug structure, which is of great significance for the precise localization and grading of prostate cancer lesions. However, the shortcomings of the existing probes in terms of targeting and metabolic safety limit the prospects for widespread application.

BRIEF SUMMARY OF THE INVENTION

In order to solve all or part of the above technical problems, the present disclosure provides the following technical solutions:

One of the purposes of the present disclosure is to provide a compound having a structural formula as follows:

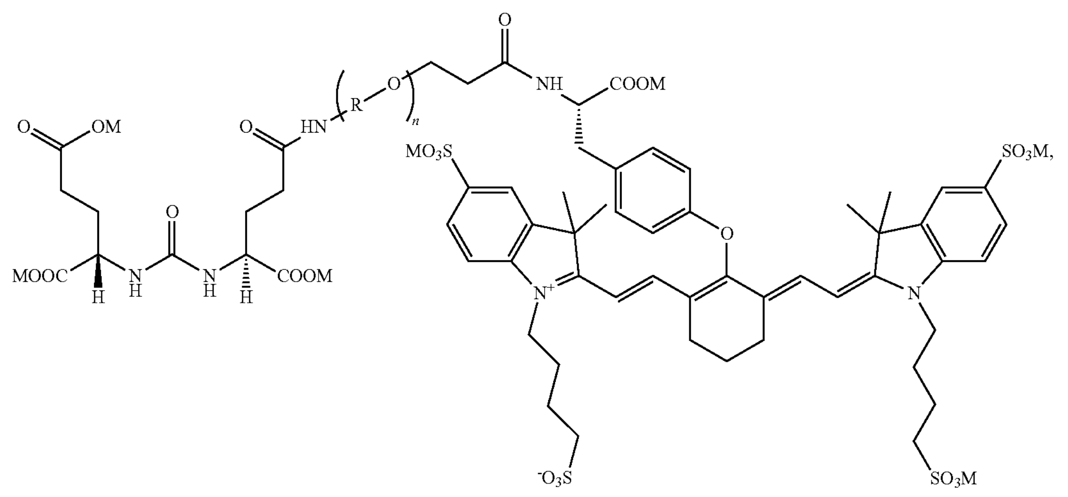

wherein cation M is selected from alkali metal cations, R is C2-C5 alkylene, and n is an integer in the range of 2-5.

In some examples, the cation M is selected from $Na^+$, $K^+$, and $Li^+$.

In some examples, a preparation method for the compound comprises the following steps:

preparing intermediate A and intermediate B, wherein intermediate A is

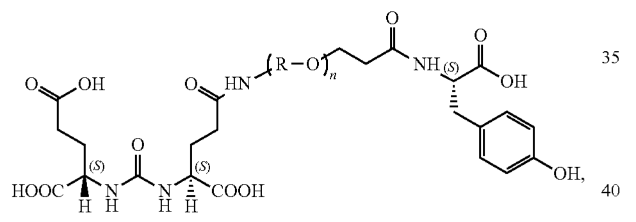

R is C2-C5 alkylene, and n is an integer in the range of 2-5; intermediate B is

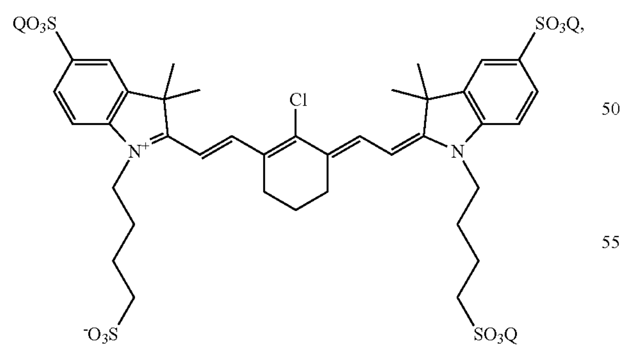

and cation Q is selected from $Na^+$, $K^+$, and $Li^+$; stirring and reacting intermediate A with intermediate B, and separating to obtain a target compound.

In some examples, the intermediate A is prepared by:

A1: preparing swollen CTC resin, reacting with Fmoc-Tyr(tBu)-OH/DIEA, and then deprotecting to obtain intermediate 1;

B1: reacting intermediate 1 with Fmoc-NH-$PEG_2$-$CH_2CH_2COOH$/HOBt after activation, and deprotecting to obtain intermediate 2;

C1: reacting intermediate 2 with compound 1/HBTU/HOBt after activation, contracting, cleaving, and deprotecting to obtain intermediate A, wherein compound 1 is

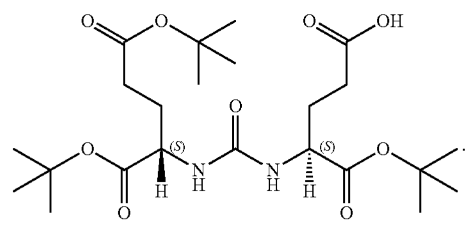

In some examples, the intermediate B is prepared by:

A2: reacting phosphorus trichloride with DMF and cyclohexanone, then mixing the resulting mixture with ice under stirring and reacting, separating a precipitate, and washing, purifying, and drying to obtain compound 2;

stirring and reacting 4-hydrazinobenzenesulfonic acid, sodium acetate, and 3-methyl-2-butanone in acetic acid under a protective gas atmosphere, then adding diethyl ether for precipitation, washing and drying to obtain compound 3; reacting the compound 3 with 1,4-butanesultone in o-dichlorobenzene under a protective gas atmosphere, then washing, separating, and drying to obtain compound 4;

B2: heating the compound 2, compound 4, and sodium acetate in methanol, then adding acetic anhydride to react, separating and purifying at room temperature to obtain intermediate B.

In some examples, the conditions for the stirring and reacting are stirring and reacting at 65-75° C. for 0.5-1.5 h. Preferably, the conditions for the stirring and reacting are stirring and reacting at 70° C. for 1 h.

Further, a composition comprises the aforementioned compound. Other auxiliary components such as water or an appropriate amount of sodium chloride may also be comprised. Auxiliary components may also comprise a carrier and the like.

Further, a kit comprises the aforementioned compound or the aforementioned composition.

In some examples, provided is a use of the aforementioned compound, the aforementioned composition, or the aforementioned kit in a fluorescent detection material. The fluorescent detection material includes but is not limited to a reagent and the like.

In some examples, provided is a use of the aforementioned compound, the aforementioned composition, or the aforementioned kit in a PSMA fluorescent detection reagent.

In some examples, provided is a use of the aforementioned compound or the aforementioned composition in a flow cytometry detection reagent.

Compared with the prior art, the present disclosure has at least the following beneficial effects: the compound and an application product thereof provided by the present disclosure have good recognition capability for a PSMA receptor, with good targeting performance. In practical applications, they can be widely used in various scenarios such as flow cytometric analysis and in vivo imaging, and have advantages in terms of fast signal response speed and high resolution. Furthermore, the compound and the application product thereof show high resolution in flow cytometry experiments and have good metabolic safety and metabolic efficiency, which is conducive to the widespread application of the product in PSMA detection technologies.

BRIEF DESCRIPTION OF THE DRAWINGS

FIG. 4A to FIG. 4F show fluorescent metabolic control imaging comparisons between the product from Example 11 of the present disclosure and the existing product OTL78: wherein FIG. 4A is a 1-hour metabolic control imaging; FIG. 4B is a 2-hour metabolic control imaging; FIG. 4C is a 4-hour metabolic control imaging; FIG. 4D is a 8-hour metabolic control imaging; FIG. 4E is a 24-hour metabolic control imaging; FIG. 4F is a 72-hour metabolic control imaging; the circled portion in each imaging is the tumor location.

DETAILED DESCRIPTION OF THE INVENTION

Figure 1:
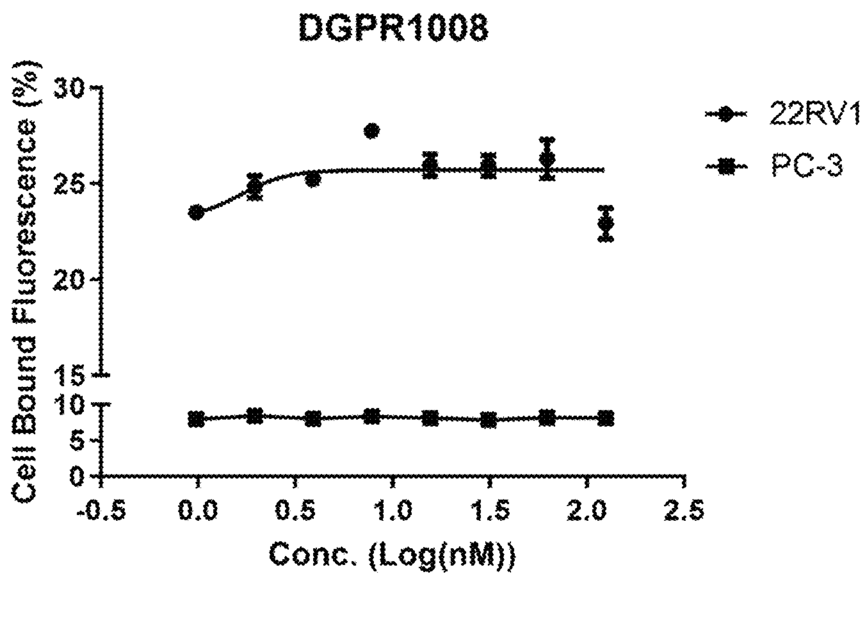
FIG. 1 shows the flow cytometry detection results according to Example 11 of the present disclosure.

The technical solutions of the present disclosure are described in detail below in conjunction with specific examples to enable those skilled in the art to better understand and implement the technical solutions of the present disclosure. The specific functional details disclosed herein should not be construed as limiting, but rather as the basis for the claims and as a representative foundation for instructing those skilled in the art to variously employ the present disclosure in virtually any appropriate detailed embodiment.

Unless otherwise specified, all raw materials and reagents used in the present disclosure are commercially available.

The OTL78 in the prior art refers to the compound in FIG. 25 of the prior art “201780067507.0”.

Including but not limited to the following examples:

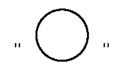

denotes a schematic representation of the carrier resin itself that does not participate in the reaction. eq refers to the molar equivalent. “V” denotes the volume-to-mass ratio. Taking the table as an example, 7V indicates that when 1 g of CTC resin was used, the corresponding reagent volume was 7 mL. Mice refer to BALB/c nude mice, 6-8 weeks old, weighing 18-20 g; rats refer to SD rats: 8 weeks old, approximately 250 g.

Example 11

Synthesis of Intermediate A

A solid-phase synthesis method was used: CTC resin was used as the solid-phase support material (1 g), which was first swollen in DMF for 1 h. 3.0 eq (in this example, eq refers to the molar multiple relative to the CTC resin, the same below) of Fmoc-Tyr(tBu)-OH was dissolved in 7V of DMF relative to the resin, then 6.0 eq (here, eq refers to the molar multiple of the CTC resin, the same below) of DIEA was added for resin loading, and the reaction was carried out for 2 h. The resin was washed with DMF 5 times, and then 6 eq (in this example, eq refers to the molar multiple relative to Fmoc-Tyr(tBu)-OH, the same below) of methanol and 10 eq (in this example, eq refers to the molar multiple relative to Fmoc-Tyr(tBu)-OH, the same below) of DIEA were added for capping. The resin was washed with DMF 4-5 times. Subsequently, a 20% piperidine/DMF solution was added to remove the N-terminal Fmoc protecting group, making the N-terminal a free amino group. The resin was washed with DMF 5-6 times to obtain intermediate 1;

3.0 eq (in this example, eq refers to the molar multiple relative to the CTC resin, the same below) of Fmoc-NH-$PEG_2$-$CH_2CH_2COOH$ was dissolved in 7V of DMF relative to the resin, then 3.0 eq of HOBt and 3.8 eq of DIC were added and activated for 5 min. The mixture was added to the resin, and the reaction was carried out under a nitrogen atmosphere for 1 h. The resin was washed with DMF 4-5 times. Subsequently, the N-terminal Fmoc protecting group was removed using 20% piperidine/DMF solution to make the N-terminal a free amino group, and the resin was washed with DMF 5 times to obtain intermediate 2;

The intermediate 1 (200 mg) obtained from the above solid-phase synthesis was placed in a three-necked flask. 3.0 eq (in this example, eq refers to the molar multiple relative to the CTC resin, the same below) of C221211A-int2 (3-BOC-DUPA) was dissolved in 7V of DMF, then 3.0 eq of HBTU, 1.5 eq of HOBt, and 4.5 eq of DIEA were added and activated for 5 min. The mixture was added to the resin, and the reaction was carried out under a nitrogen atmosphere for 1 h. The resin was washed with DMF 4-5 times;

Methanol was added for concentration, and the product was dried.

The target polypeptide was cleaved from the resin and the side-chain protecting groups were removed using a cleavage solution (trifluoroacetic acid: $H_2O$:triisopropylsilane=90:5:

5, v/v) (reacted at 20-30° C. for 3 h). The mixture was subjected to suction filtration. The filtrate was added to methyl tert-butyl ether, and a precipitate was precipitated. The suspension was centrifuged to obtain a crude product of C221211A-19, which was subjected to preparative separation and lyophilized to obtain C221211A-19 (70 mg), i.e., intermediate A.
Purity: 62.18%, LCMS: $[M+H]^+$=643.2.
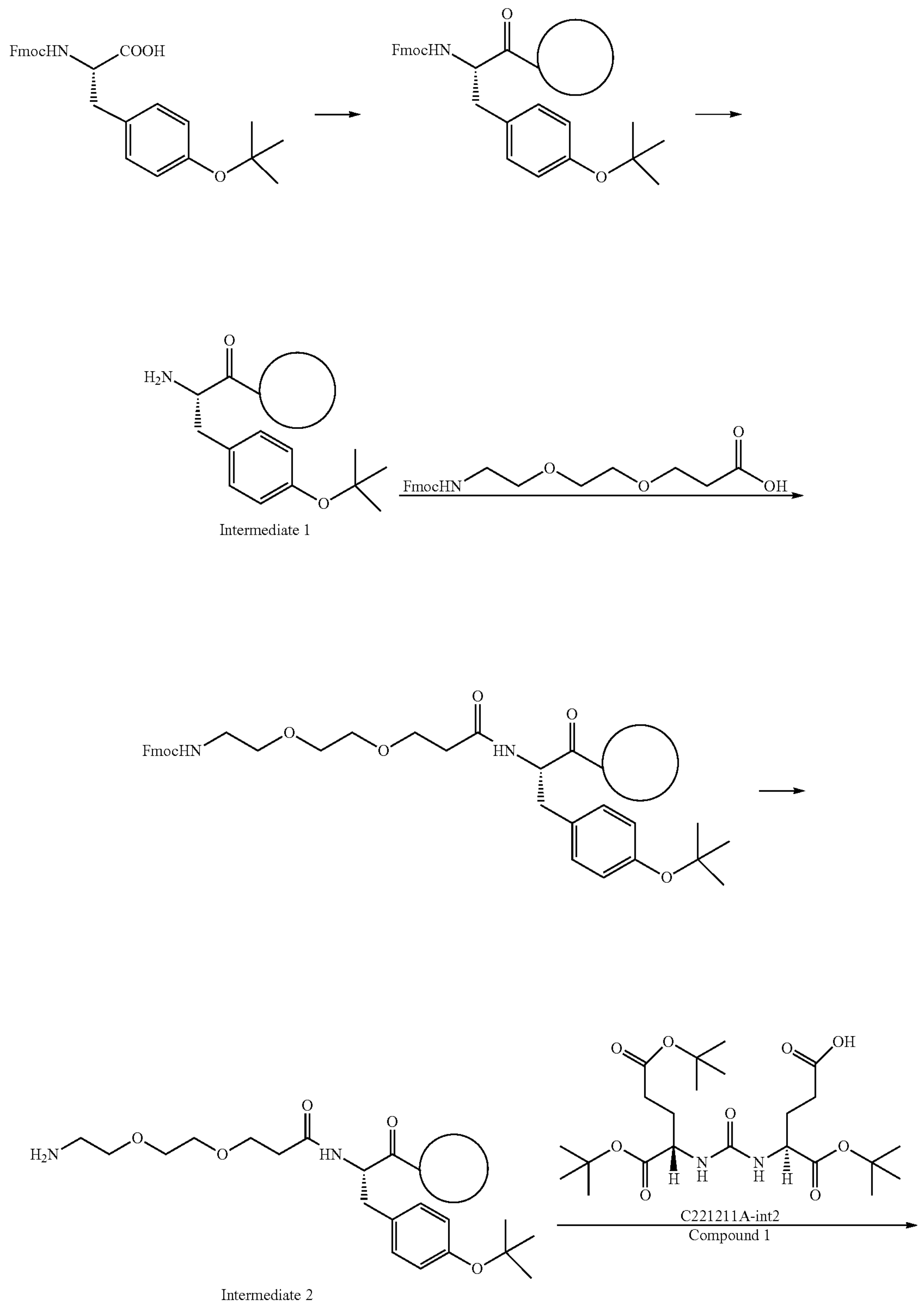

-continued

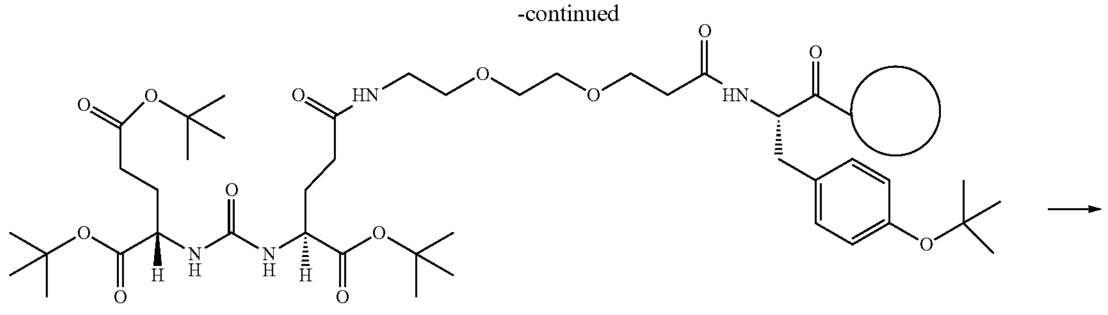

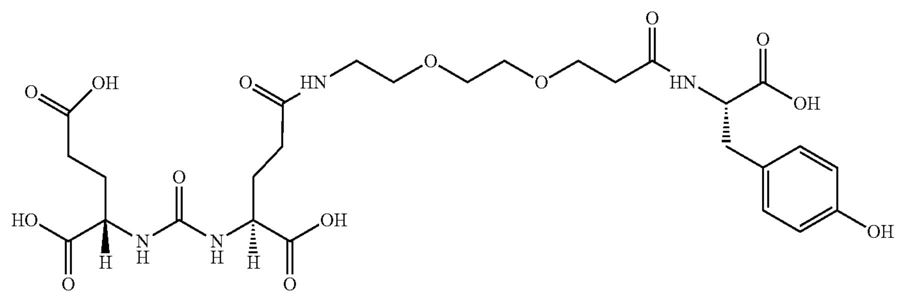

C221211A-19
Intermediate A

Synthesis of Intermediate B (dye) Synthesis of Compound 2: (E)-2-chloro-3-(hydroxymethylene) cyclohex-1-enecarbaldehyde (I)

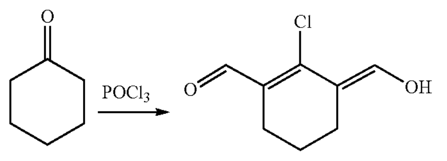

At 0° C., phosphorus oxychloride (35.0 mL, 58.8 g, 0.38 mol) was added dropwise to a dry flask containing anhydrous DMF (50 mL). The mixture was stirred for 30 min, followed by the addition of cyclohexanone (10.5 mL, 9.98 g, 0.10 mol), heated to 50° C. and reacted for 6 h. Subsequently, the red mixture was poured into 150 g of ice and stirred for 5 h. The yellow precipitate was collected, washed with water, and purified with $CH_2Cl_2$. After filtration, the product was collected and dried under vacuum to obtain compound 2 (13.5 g, 78.4 mmol, yield: 77%). LCMS m/z=173 $(m+H)^+$.

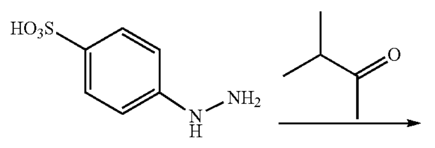

-continued

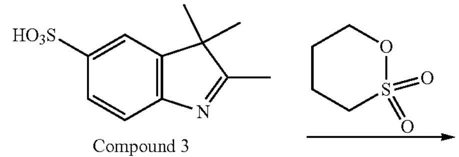

Compound 3

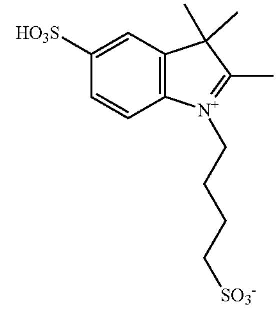

Compound 4

Synthesis of Compound 3: Chemical Name: 2,3,3-Trimethyl-3H-indole-5-sulfonic Acid (II)

4-Hydrazinobenzenesulfonic acid (10.00 g, 53.2 mmol), sodium acetate (8.72 g, 106.4 mmol), 3-methyl-2-butanone (16.80 mL, 13.50 g, 156.80 mmol), and glacial acetic acid (60 mL) were sequentially added. The mixture was stirred at 130° C. under an argon atmosphere for 5 h. After cooling to room temperature, ether was added to precipitate the product. The mixture was filtered and dried under vacuum to obtain compound 3 (11.2 g, 46.8 mmol, 88%). LCMS: m/z=240, $(m+H)^+$.

Synthesis of Compound 4: 5-Sulfo-1-(4-sulfobutyl)-2,3,3-trimethyl-3H-indolium Betaine (III)

Compound 3 (5.00 g, 20.92 mmol) and 1,4-butanesultone (4.91 mL, 6.54 g, 48.11 mmol) were added to 1,2-dichlorobenzene (125 mL). The mixture was stirred and reacted at 110° C. under an argon atmosphere for 12 h. After cooling to room temperature, deionized water was added to the reaction mixture to dissolve the solid. The aqueous phase was washed with $CH_2Cl_2$, and the organic layer was discarded. The remaining aqueous phase was lyophilized.

Compound 4 (5.21 g, 13.89 mmol, yield: 66%) was obtained. LCMS: m/z=375.9, $(m+H)^+$.

Synthesis of Intermediate B (Dye)

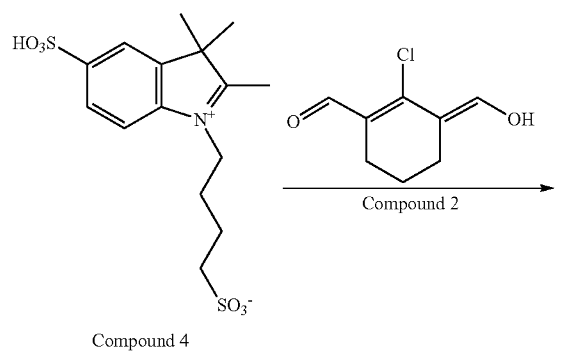

Compound 4

-continued

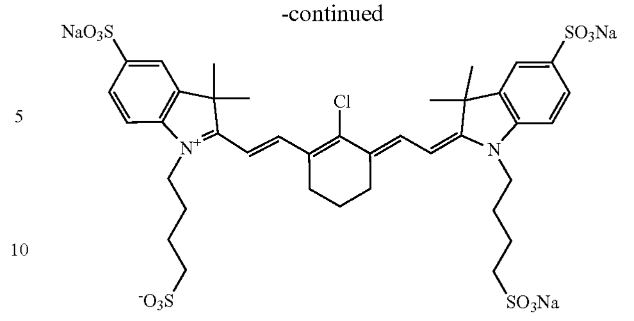

Intermediate B

Compound 4 (3.00 g, 8.00 mmol), compound 2 (688 mg, 4.00 mmol), and sodium acetate (656 mg, 8.00 mmol) were heated to 70° C. in methanol (80 mL). Acetic anhydride (80 mL) was added, and the mixture was stirred for 8 h. After cooling to room temperature, ether was added to the mixture to precipitate. The solid precipitate was collected by filtration, dissolved in deionized water, and precipitated with 2-propanol. The solid was collected by filtration, and the process was repeated twice. After drying under vacuum, the (dye) intermediate B (1.18 g, 1.33 mmol, 33%) was obtained. LC-MS m/z: 886.8 $(M)^+$.

$^1H$ NMR (400 MHz, $D_2O$): δ=8.35 (d, J=14.0 Hz, 2H), 7.88 (s, 2H), 7.79 (d, J=8.4 Hz, 2H), 7.34 (d, J=8.4 Hz, 2H), 6.25 (d, J=14.0 Hz, 2H), 4.17 (s, 4H), 3.07-2.86 (m, 4H), 2.59 (s, 4H), 2.03-1.76 (m, 10H), 1.72 (s, 12H).

Synthesis of DGPR1008:

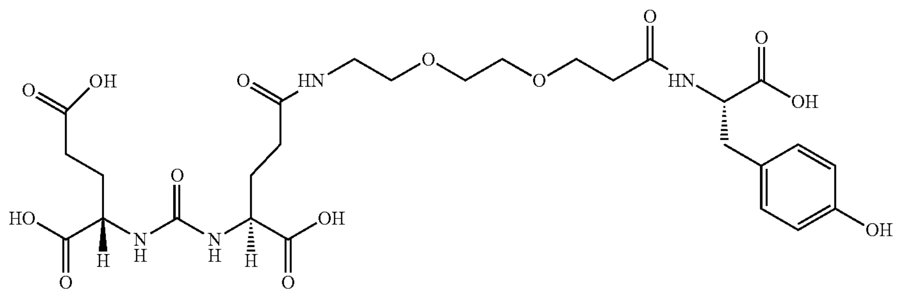

C221211A-19

+

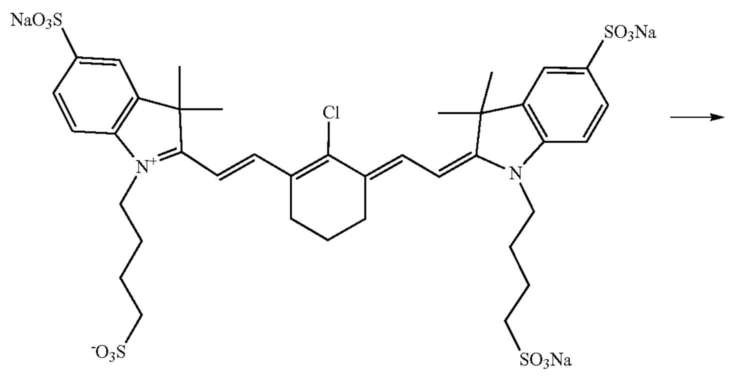

dye

-continued

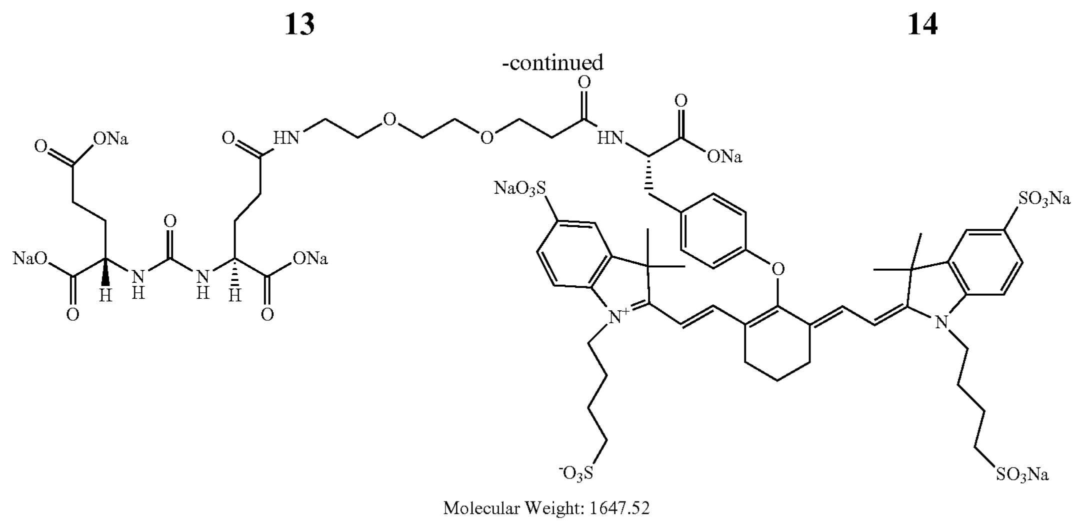

Molecular Weight: 1647.52

C221211A-19 (68.6 mg, 0.1068 mmol) and C221211A-int1 (dye) (104.2 mg, 0.1068 mmol) were placed in a 25 mL single-necked flask. $Na_2CO_3$ (67.8 mg, 0.6403 mmol) was dissolved in purified water (40 V relative to the resin) and added to the reaction flask. The mixture was stirred at 70° C. for 1 h. A sample was taken for HPLC analysis, showing RT=6.930 with a purity of 40.52%. The reaction mixture was subjected to preparative purification with a mobile phase of 0.5% ammonium bicarbonate in methanol/water solution, followed by lyophilization to obtain 69.2 mg of the product.

$^1H$ NMR (400 MHz, D2O) δ 7.92 (s, 2H), 7.79 (s, 4H), 7.43-7.22 (m, 4H), 7.19-7.02 (m, 2H), 6.29-6.09 (m, 1H), 4.52-4.33 (m, 1H), 4.23-3.97 (m, 6H), 3.64-3.14 (m, 13H), 3.04-2.56 (m, 9H), 2.48-2.33 (m, 4H), 2.33-2.23 (m, 2H), 2.19-1.99 (m, 2H), 1.99-1.70 (m, 12H), 1.43-1.30 (m, 12H).

Product Testing:

1. Receptor Binding was Detected by Flow Cytometry In Vitro:

Experimental Principle

Prostate-specific membrane antigen (PSMA) is overexpressed on prostate cancer cells. Both DUPA-FITC and DGPR1008 are capable of targeting the PSMA receptor in prostate cancer cells, with the difference being that DUPA-FITC is connected to a visible light dye (Ex=495 nm, Em=520 nm), whereas DGPR1008 is connected to a near-infrared dye (Ex=776 nm, Em=793 nm). Since the majority types of lasers equipped in flow cytometers operate within the visible light spectrum, the binding affinity of DGPR1008 to the receptor can not be directly measured. Therefore, the competitive binding of DGPR1008 with DUPA-FITC to PSMA is employed to indirectly assess the binding affinity of the test compound to the receptor.

Experimental Materials

DGPR1008, DUPA-FITC, 22RV1 (PSMA+), PC3 (PSMA−), 1640 culture medium, FBS, double antibiotics, trypsin, centrifuge, 4° C. constant temperature incubator, flow cytometer.

Experimental Method:

Drug preparation: 100 nmol/L DUPA-FITC was prepared using culture medium. The test compound was diluted to nine concentrations (0.00098 μM, 0.002 μM, 0.008 μM, 0.01 μM, 0.03 μM, 0.05 μM, 0.09 μM, 0.1 μM, and 0.125 μM) using culture medium containing 100 nmol/L DUPA-FITC, with three replicate wells for each concentration.

Cell culture: The cells were seeded in T75 culture flasks. After 48 h, cells in the logarithmic growth phase were taken, digested with trypsin for 1-2 min, and the digestion was then terminated by adding fresh culture medium. After cell counting, the cells were transferred into a 96-well plate ($1\times10^5$ cells/well), totaling 27 wells. The culture medium was discarded by centrifugation (800 rpm, 5 min), and the cells were washed twice with PBS and then centrifuged to collect the cell pellet. The prepared culture media with 9 concentrations were added to the cell-containing wells, with three replicates for each concentration. The cells were incubated at 4° C. in the dark for 30 min, and then the culture medium in the wells was discarded. Cells were washed by adding 300 μL of fresh culture medium (twice) and saline (once) to each well, followed by resuspension in 300 μL of saline for flow cytometry detection.

The experiment demonstrated that, as shown in FIG. 1, the negative cell line PC3 had no binding ability to PSMA receptor, the positive cell 22RV1 had a certain binding ability to PSMA receptor, and the target compound showed good affinity.

2. Drug Efficacy Validation Experiment Using In Vivo Live Imaging

Experimental Principle

Prostate-specific membrane antigen (PSMA) is overexpressed on prostate cancer cells. The test compound is a PSMA-targeting molecule conjugated with a near-infrared region I dye. The test compound can bind to PSMA and "illuminate" cancer cells upon excitation by a near-infrared light source. In this experiment, the in vivo tissue distribution of the test compound in mice is detected using in vivo live imaging.

Experimental Materials

DGPR1008, 22RV1 (PSMA+), PC3 (PSMA−), 1640 culture medium, FBS, double antibodies, trypsin, Matrigel (BD), vernier caliper, centrifuge, IVIS live imager.

Experimental Method

Cell Line: 22RV1 (PSMA+)

Matrigel was thawed on ice in advance, and the culture medium was pre-cooled on ice. After centrifugation, the cells were resuspended in the pre-cooled culture medium, followed by the addition of HC Matrigel gel in a volume equal to the culture medium. The centrifuge tube containing the cells was placed on ice and transferred to the animal facility. The cells were thoroughly dispersed before inoculation. The right dorsal shoulder area of the mice was disinfected with an alcohol cotton ball, and a single intravenous administration was performed with an inoculation volume of 200 μL per mouse. All operations were performed on ice. When the tumor volume reached 300-400 $mm^3$, the mice were grouped for administration. Nine mice with well-grown and regularly shaped tumors were selected into the group. The nine mice were randomly divided into three groups: G1 (25 nmol/mouse), G2 (50 nmol/mouse), and G3 (100 nmol/mouse), with three mice in each group. The scanning time: 1, 2, 4, 8, 24, and 48 h.

Figure 2:
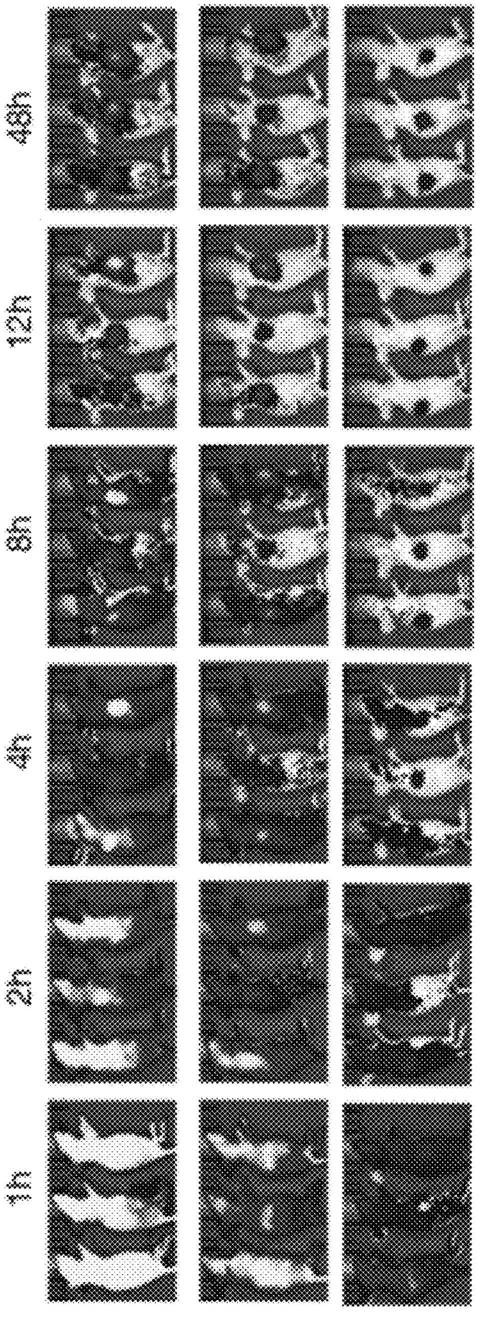
FIG. 2 is a fluorescent metabolic map according to Example 11 of the present disclosure.
Figure 3A:
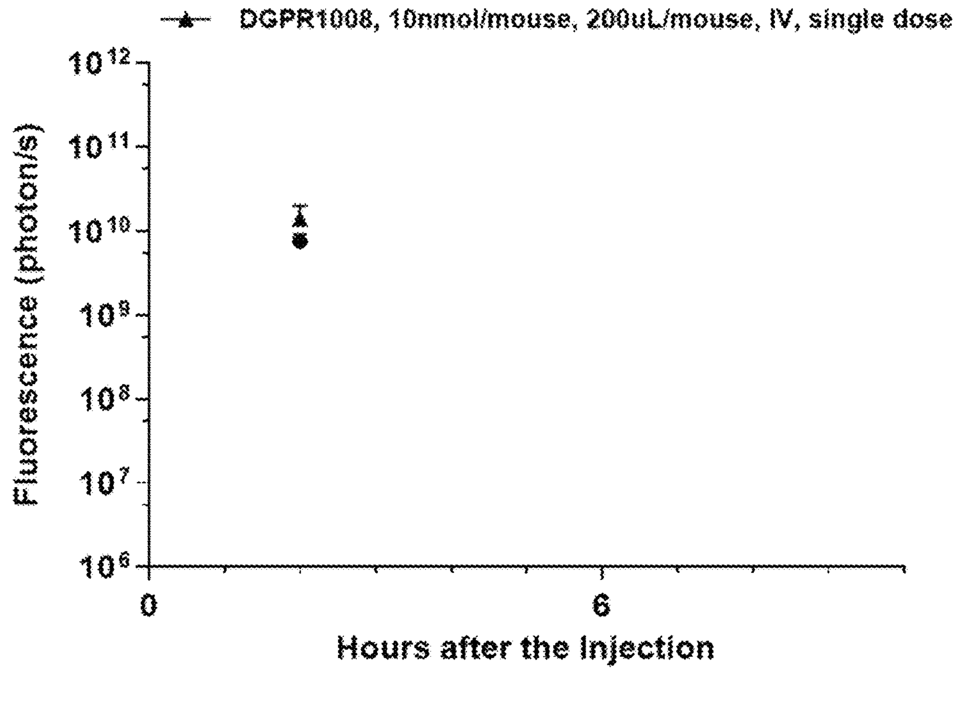
FIG. 3A and FIG. 3B are control charts of the product from Example 11 according to the present disclosure and the existing product OTL78.
Figure 3B:
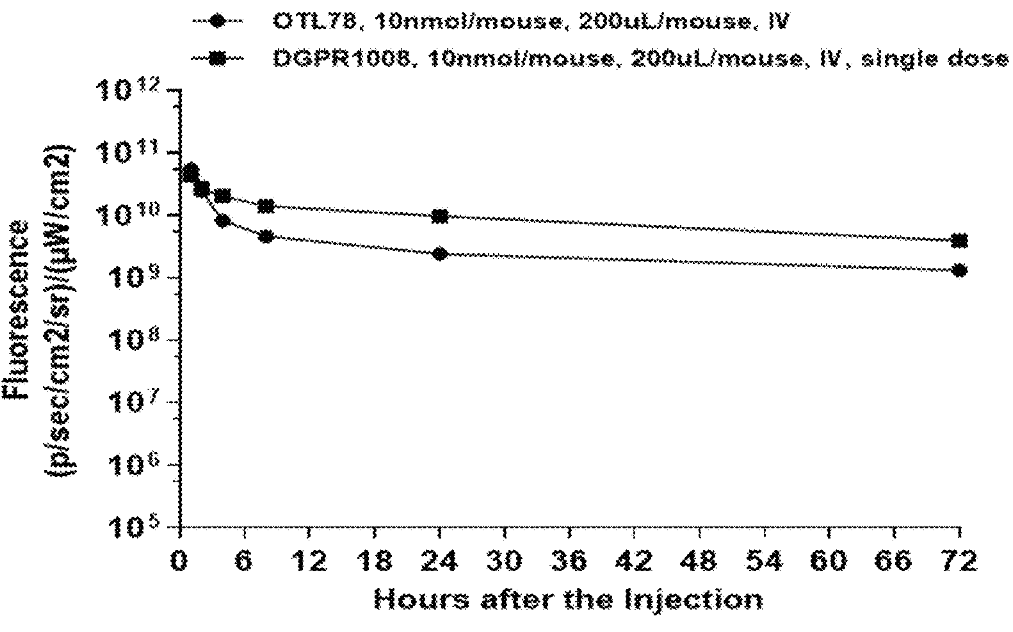
Figure 4A:
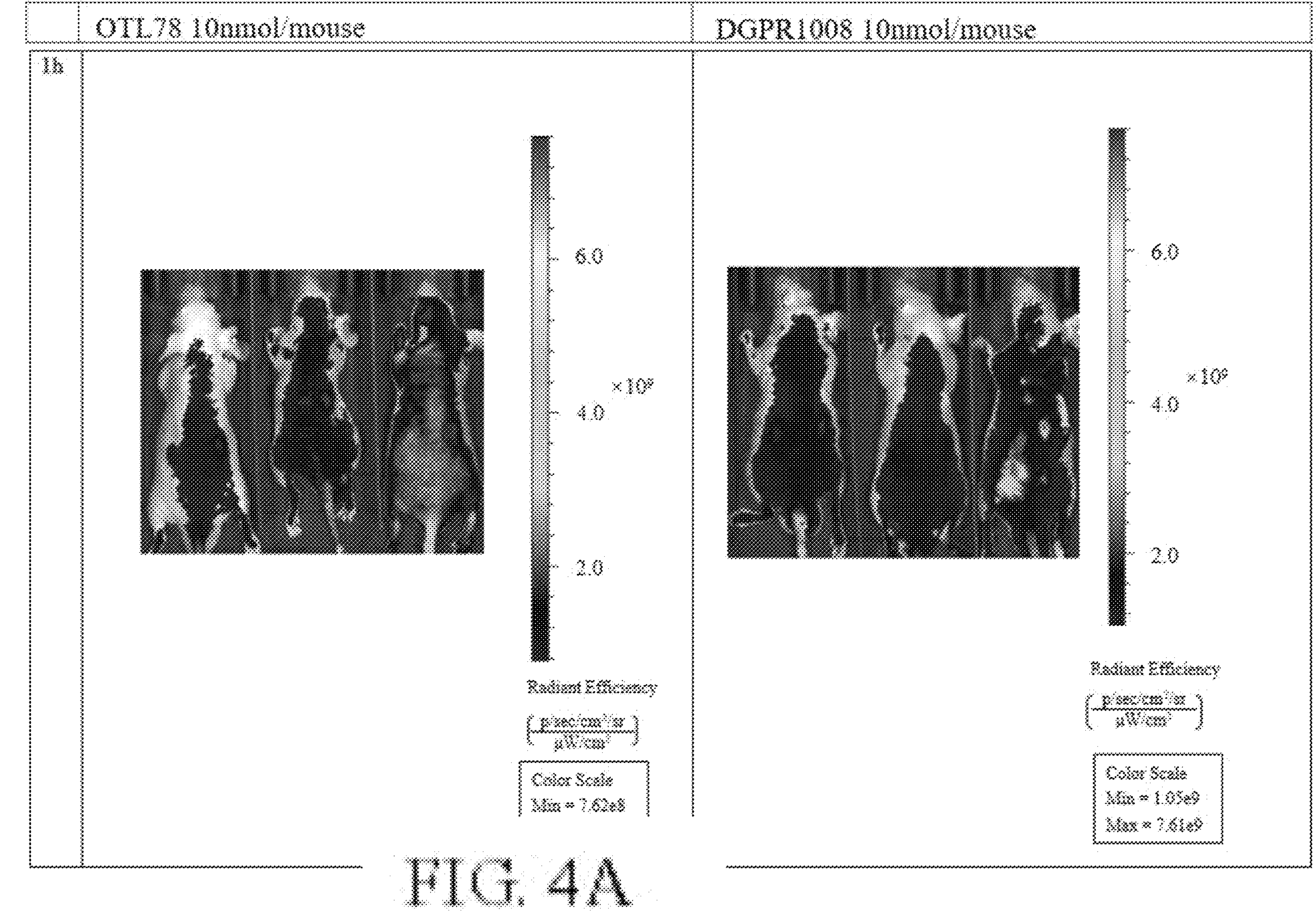
Figure 4B:
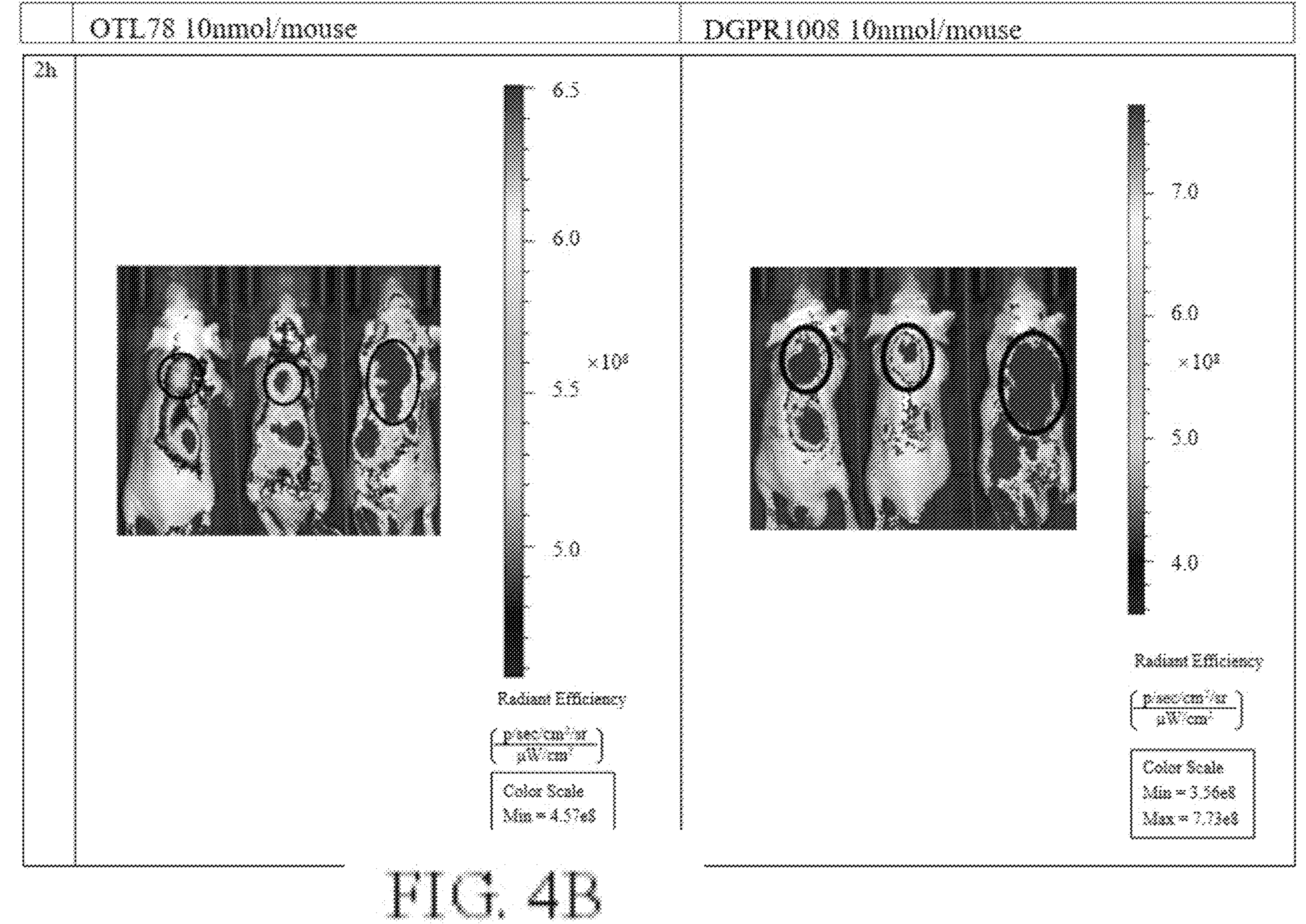
Figure 4C:
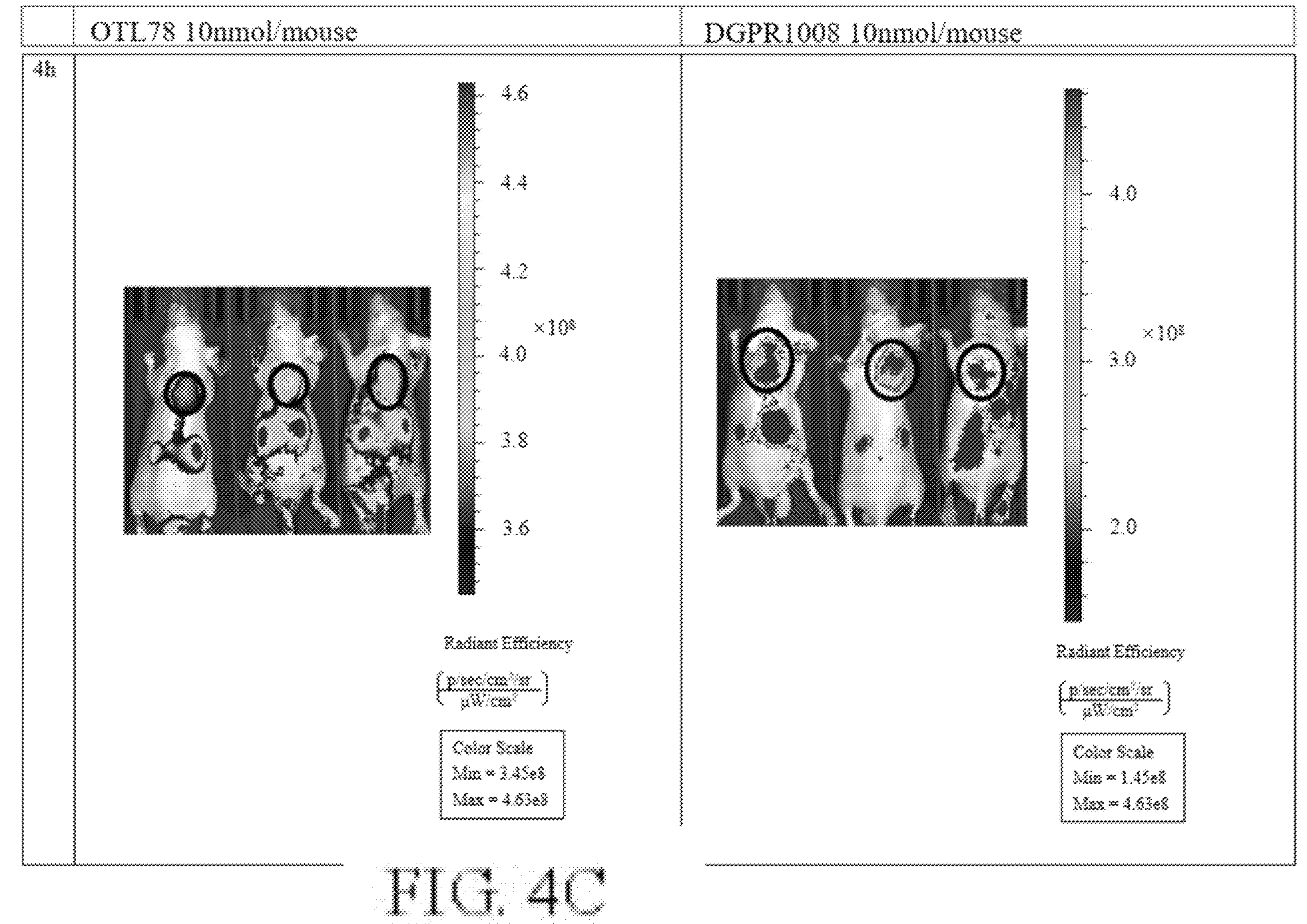
Figure 4D:
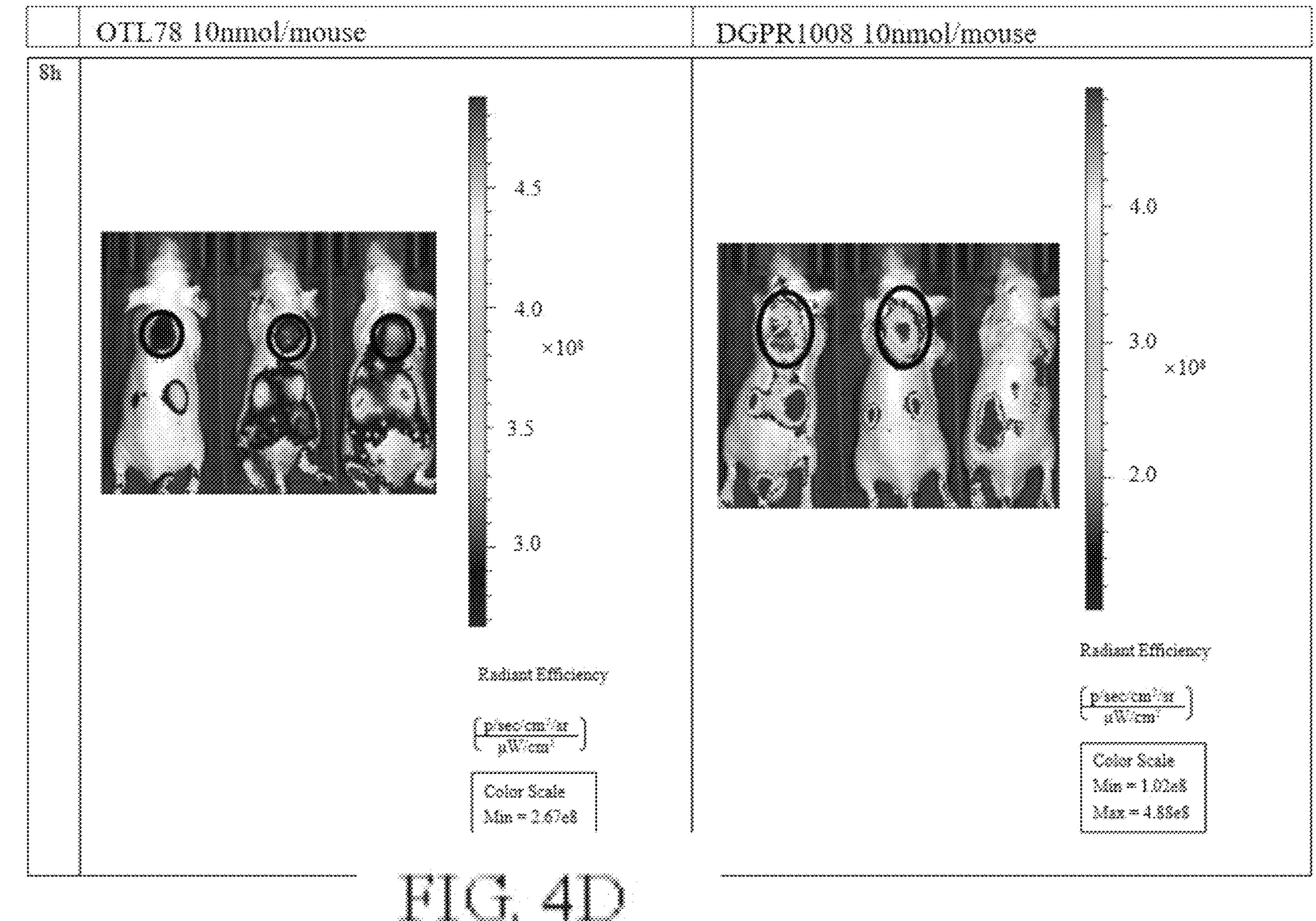
Figure 4E:
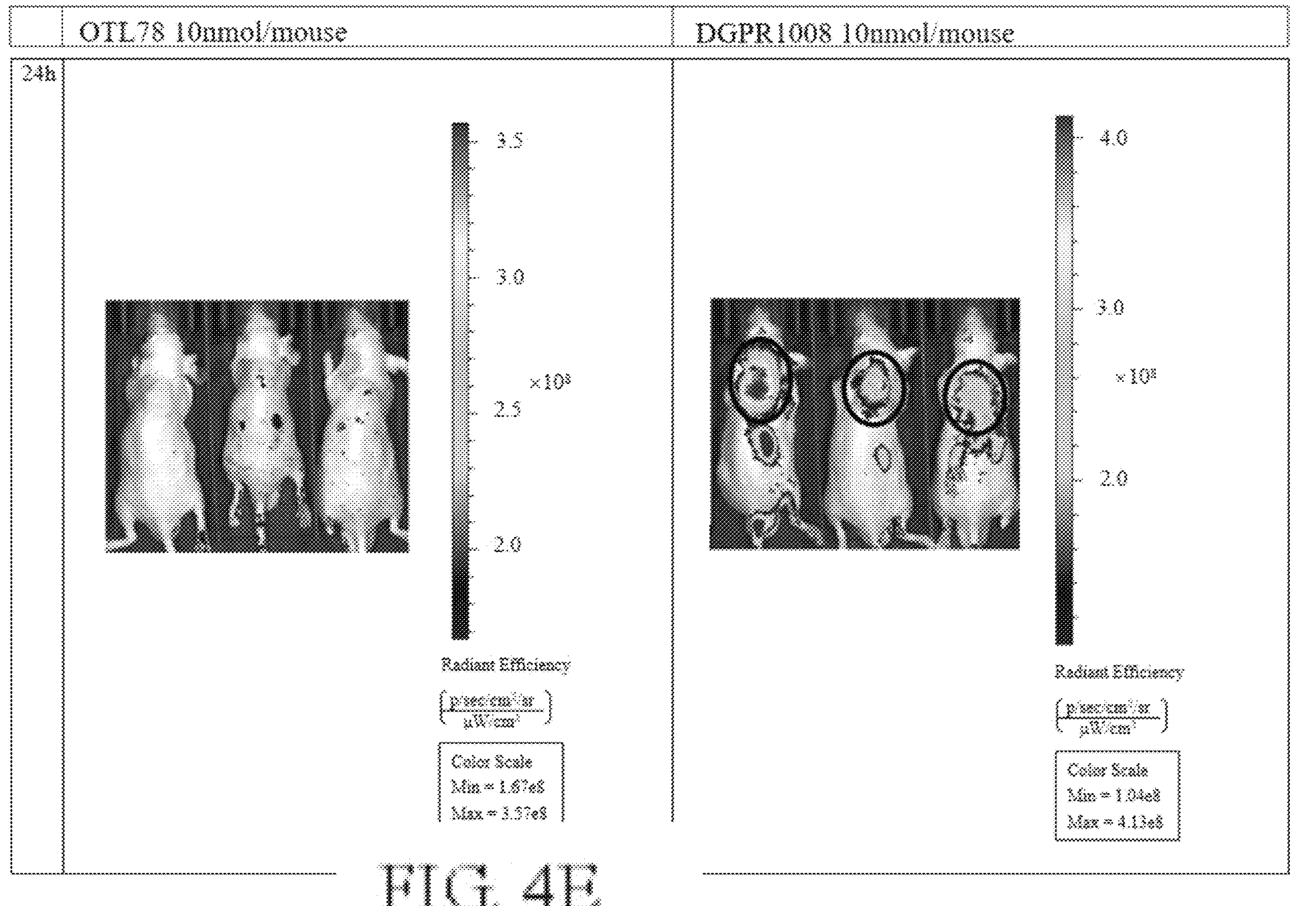
Figure 4F:
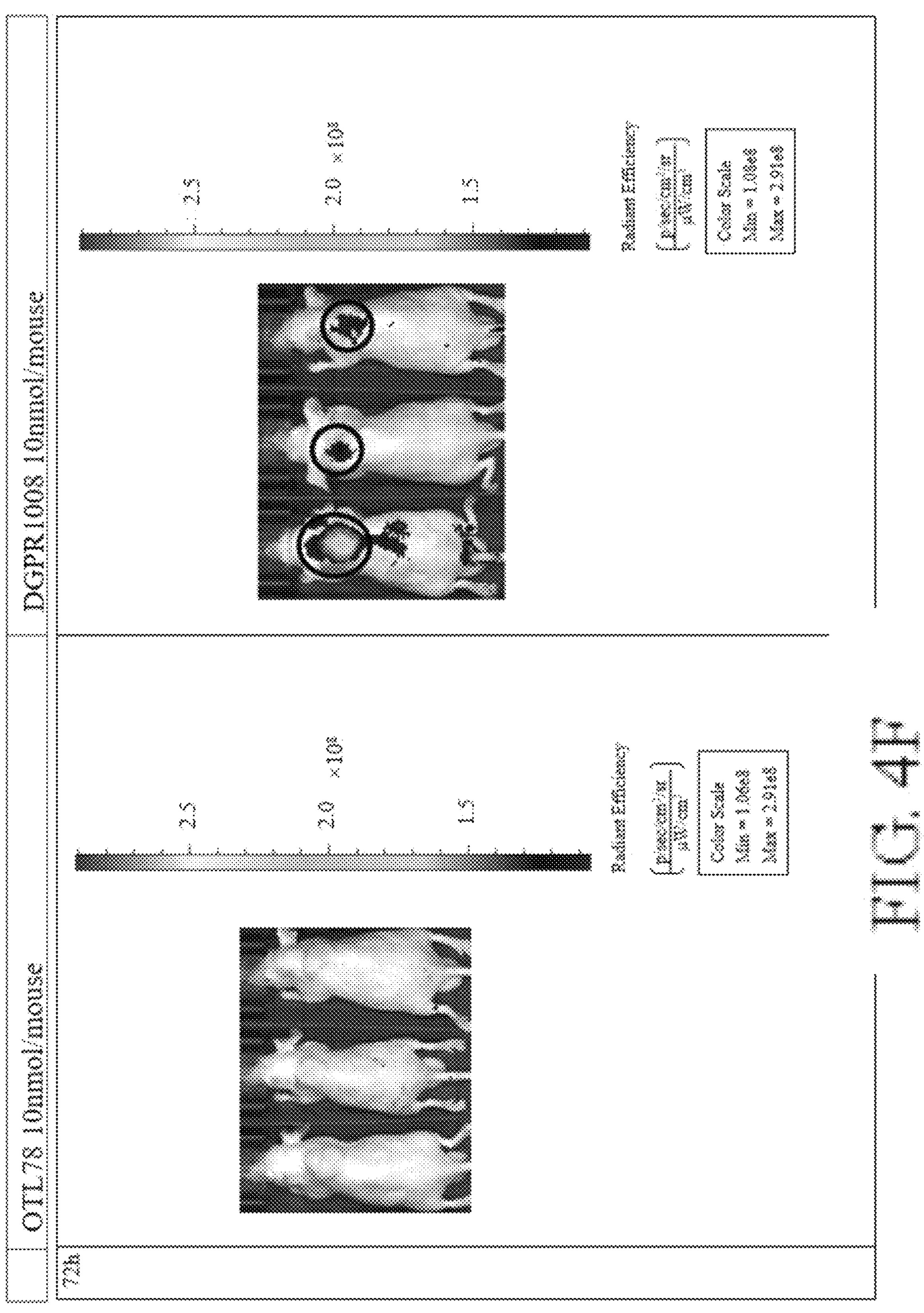

The experiment demonstrated that, as shown in FIG. 2, the target compound could be enriched in the prostate cancer tumor site within a certain period of time at the aforementioned high, medium, and low doses. The compound DGPR1008 showed good targeting properties.

3. Comparison with the Existing Product OTL78

Experimental Principle

The Prostate-specific membrane antigen (PSMA) is overexpressed on prostate cancer cells. The test compound is a PSMA-targeting molecule conjugated with a near-infrared region I dye. The test compound can bind to PSMA and "illuminate" cancer cells upon excitation by a near-infrared light source. In this experiment, the in vivo and ex vivo tissue distribution of the test compound in mice is detected using in vivo live imaging.

Experimental Materials

DGPR1008, 22RV1 (PSMA+), BALB/c nude mouse, 1640 culture medium, FBS, double antibodies, trypsin, Matrigel (BD), vernier caliper, centrifuge, IVIS live imager.

Experimental Method

Cell Line: 22RV1 (PSMA+)

Matrigel was thawed on ice in advance, and the culture medium was pre-cooled on ice. After centrifugation, the cells were resuspended in the pre-cooled culture medium, followed by the addition of HC Matrigel gel in a volume equal to the culture medium. The centrifuge tube containing the cells was placed on ice and transferred to the animal facility. The cells were thoroughly dispersed before inoculation. The back of the neck was disinfected with an alcohol cotton ball, and a single intravenous administration was performed with an inoculation volume of 200 μL per mouse. All operations were performed on ice. When the tumor volume reached 300-400 $mm^3$, the mice were grouped for administration. Six mice with well-grown and regularly shaped tumors were selected into the group. The six mice were randomly divided into two groups: G1 (OTL78 10 nmol/mouse) and G2 (DGPR1008 10 nmol/mouse) with three mice in each group. The scanning time: 1, 2, 4, 8, 24, and 72 h.

(1) Results and Data of In Vivo Live Imaging of Drug Efficacy (Mice were Used as Experimental Subjects in this Part)

As shown in FIG. 3A, FIG. 3B, and FIG. 4A to FIG. 4F, the in vivo live imaging data of OTL78 and DGPR1008 were compared:

| Time/h | OTL78 10 nmol/mouse | DGPR1008 10 nmol/mouse |
|---|---|---|
| 1 | 8.75E+09 | 2.18E+10 |
| 2 | 6.58E+09 | 1.15E+10 |
| 4 | 3.27E+09 | 6.43E+09 |
| 8 | 1.71E+09 | 3.51E+09 |

-continued

| Time/h | OTL78 10 nmol/mouse | DGPR1008 10 nmol/mouse |
|---|---|---|
| 24 | 1.41E+09 | 3.96E+09 |
| 72 | 9.69E+08 | 3.17E+09 |
| Blank | 9.76E+07 | |

It can be observed from the images and data that:

1) At each time point, the fluorescence value of DGPR1008 at the tumor site is higher than that of OTL78;

2) The compound of this example shows good TBR (tumor-to-background ratio) from about 2 h to 72 h.

(2) Results of 2-Hour Ex Vivo Tissue Distribution:

Fluorescence Ratio of Tumor to In Situ Normal Prostate:

| Group | Animal No. | Tumor | Prostate | T/P Ratio |
|---|---|---|---|---|
| Group-1 OTL78, | 94771 | 7.07E+09 | 4.77E+08 | 14.8 |
| 10 nmol/mouse, | 94776 | 1.01E+10 | 8.11E+09 | 1.25 |
| 200 μL/mouse | 94778 | 4.61E+09 | 1.23E+09 | 3.75 |
| | Mean | 7.26E+09 | 3.27E+09 | 6.61 |
| | SD | 2.75E+09 | 4.21E+09 | |
| Group-2 DGPR1008, | 94772 | 1.09E+10 | 2.17E+08 | 50.2 |
| 10 nmol/mouse, | 94779 | 8.18E+09 | 2.41E+08 | 33.9 |
| 200 μL/mouse | 94780 | 9.42E+09 | 5.96E+08 | 15.8 |
| | Mean | 9.50E+09 | 3.51E+08 | 33.3 |
| | SD | 1.36E+09 | 2.12E+08 | |

Fluorescence unit: photon/second (3) Results of TBR (Mean)

| Group | TBR | | | | | |
|---|---|---|---|---|---|---|
| | 1 h | 2 h | 4 h | 8 h | 24 h | 72 h |
| Group-1 OTL78, 10 nmol/mouse, 200 μL/mouse | 1.30 | 1.35 | 1.38 | 1.36 | 1.55 | 1.65 |
| Group-2 DGPR1008, 10 nmol/mouse, 200 μL/mouse | 1.33 | 1.64 | 1.83 | 1.74 | 2.04 | 1.97 |

Conclusion

1) As can be seen from the above table, when the compound of this example is used as a recognition auxiliary, there is a significant signal intensity ratio between tumor and normal prostate tissues, which can fully reflect the ability of the drug to distinguish between normal prostate and diseased prostate;

2) Compared with OTL78, DGPR1008 in this example exhibits stronger discrimination capability (approximately 5-fold) and higher TBR. The higher TBR can make the tumor boundary line clearer during surgery and obtain more accurate resection margins.

3) It can be seen from the pharmacokinetic parameters of 2 mg/kg plasma in rats, the average $AUC_{0-t}$ of OTL78 is 9429 ng·h/mL, the average clearance of OTL78 is 3.50 mL/min/kg, while the average $AUC_{0-t}$ of DGPR1008 is 6208 ng·h/mL, the average clearance of DGPR1008 in this example is 5.23 mL/min/kg, indicating that DGPR1008 is cleared more rapidly in rats in vivo, thereby correspondingly increasing its safety factor.

4) In the acute toxicity experiment on rats, no toxic reactions were observed in the three dose groups of high, medium, and low doses, demonstrating the excellent safety of the compound DGPR1008 in this example.

Conclusion: The compound in this example exhibits a high signal-to-noise ratio in fluorescence imaging applications—indicating more sensitivity during surgery; and rapid clearance—indicating faster clearance post-surgery and superior safety advantages.

Example 12

The difference from Example 11 was only in:

Intermediate B

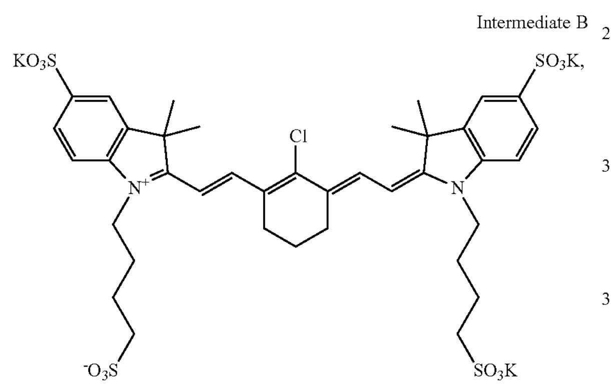

while the remaining corresponding reagents were adaptively adjusted by those skilled in the art.

The target compound prepared in this example was

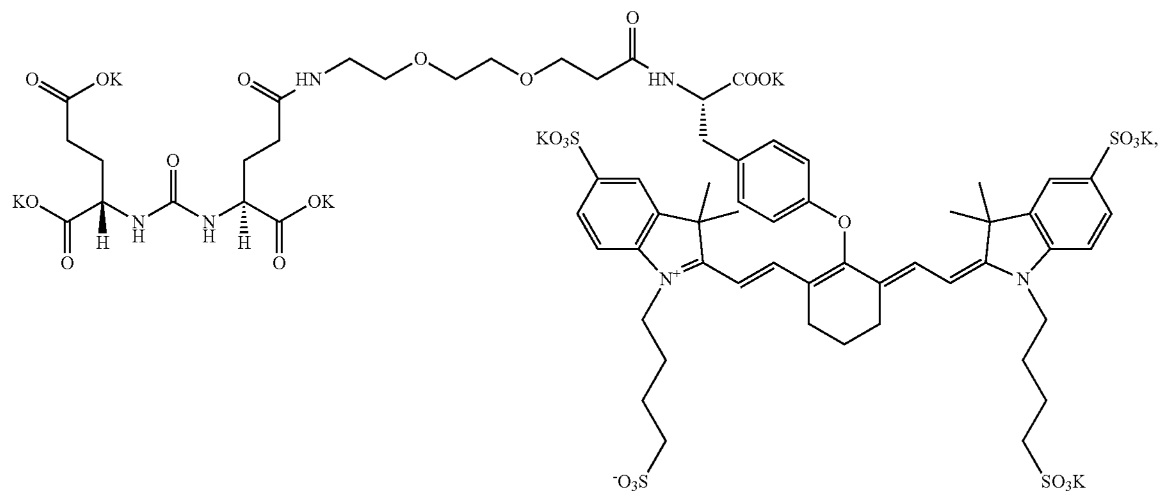

which was detected using the experimental method demonstrated in Example 11: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications-indicating more sensitivity during surgery; and rapid clearance-indicating faster clearance post-surgery and superior safety advantages.

Example 13

The difference from Example 11 was only in:

Intermediate B

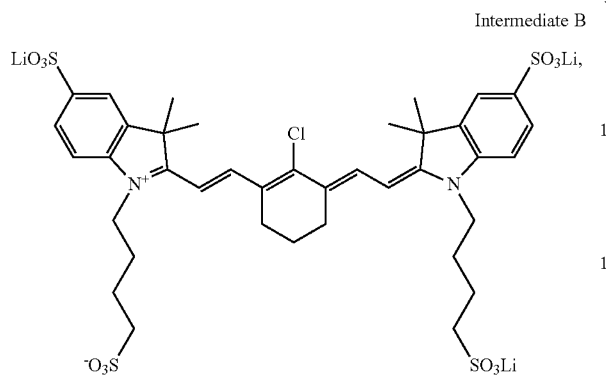

while the remaining corresponding reagents were adaptively adjusted by those skilled in the art.

The target compound prepared in this example was

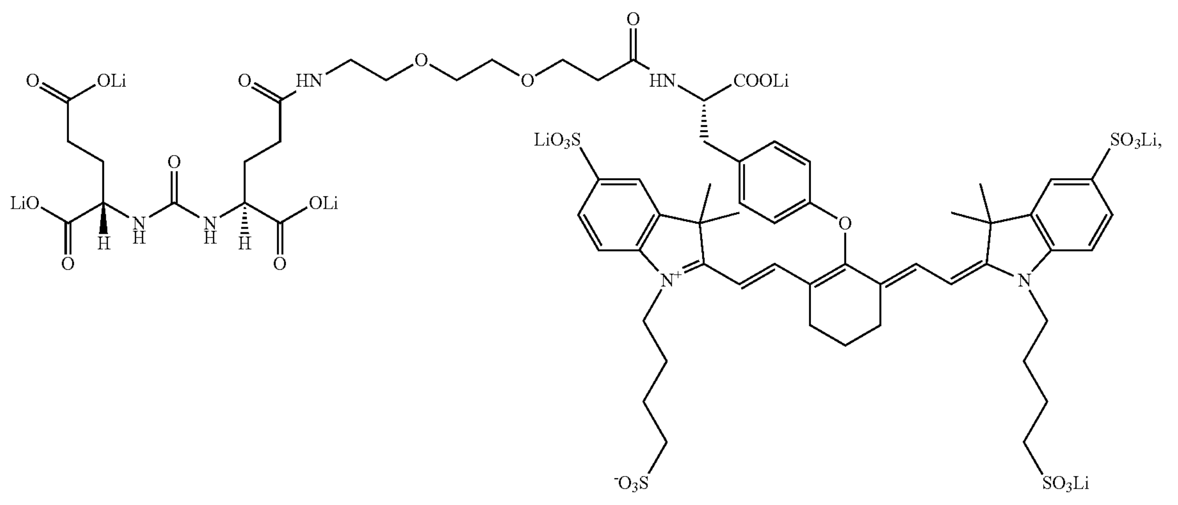

which was detected using the experimental method demonstrated in Example 11: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications—indicating more sensitivity during surgery; and rapid clearance—indicating faster clearance post-surgery and superior safety advantages.

Intermediate 1 (including but not limited to those used in the examples below) can be realized by technical means including but not limited to those listed in Example 11.

Example 21
The target compound prepared in this example was:
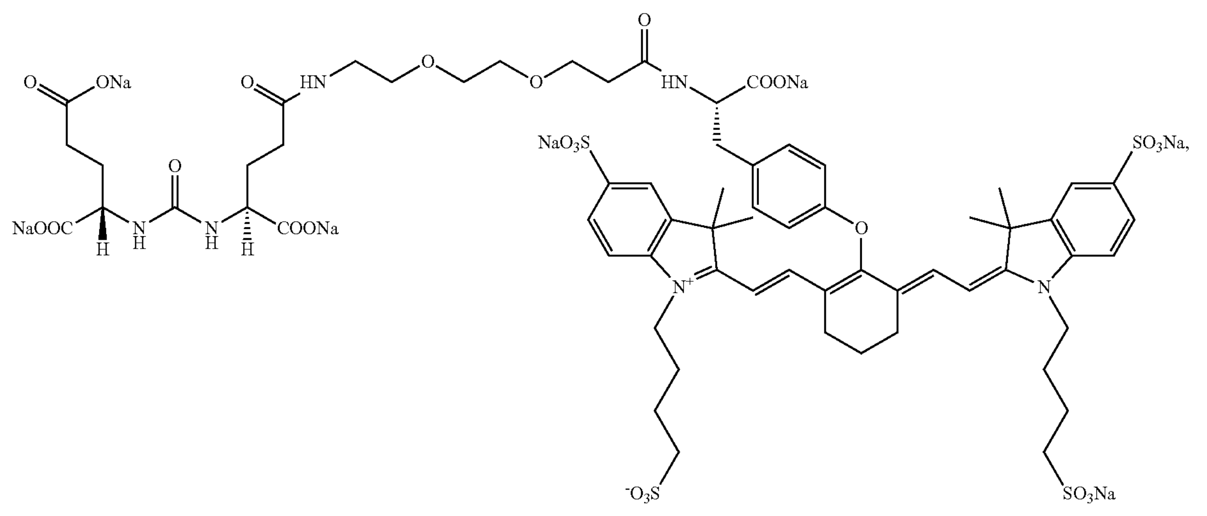
The preparation procedure was as follows:
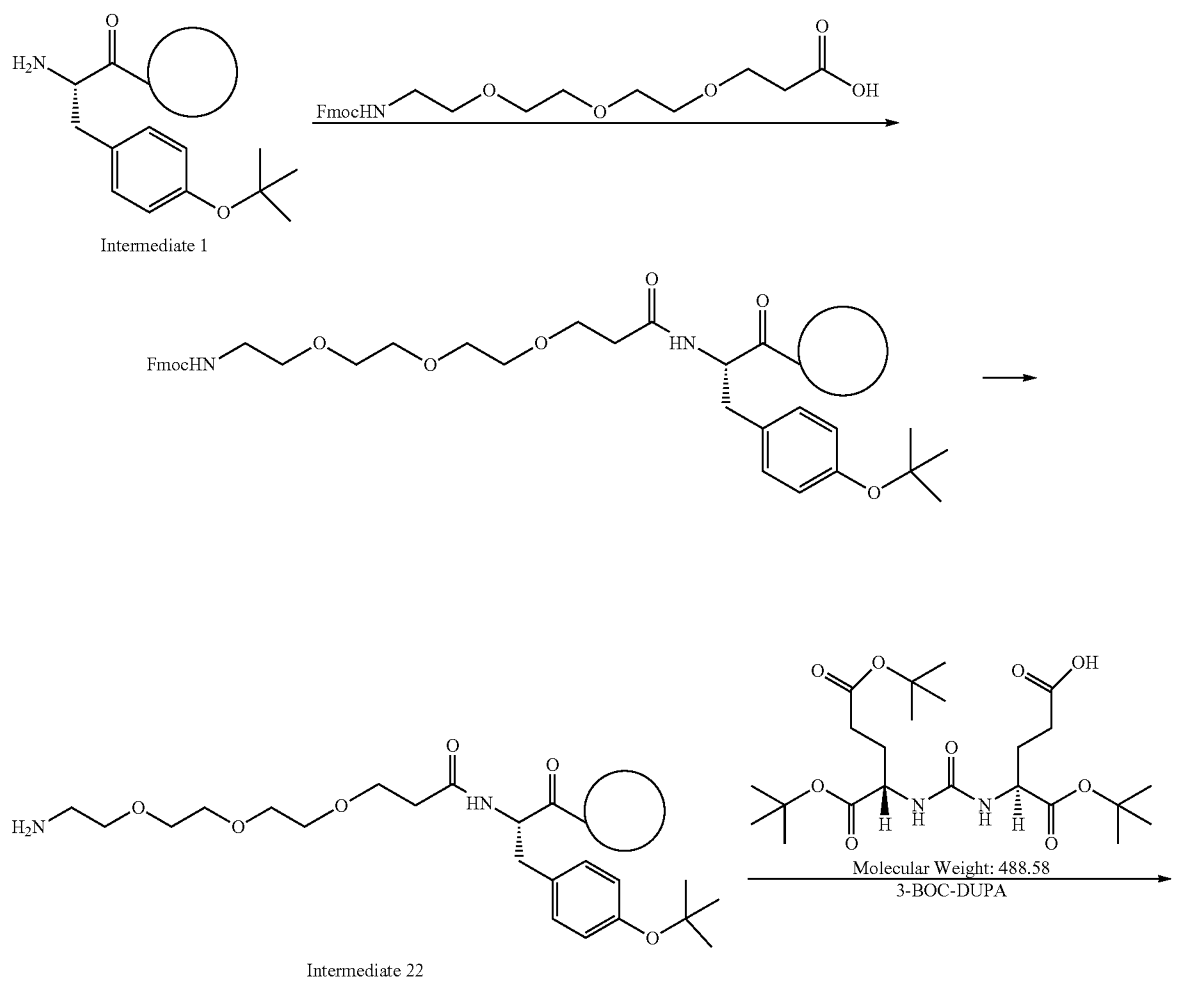

-continued

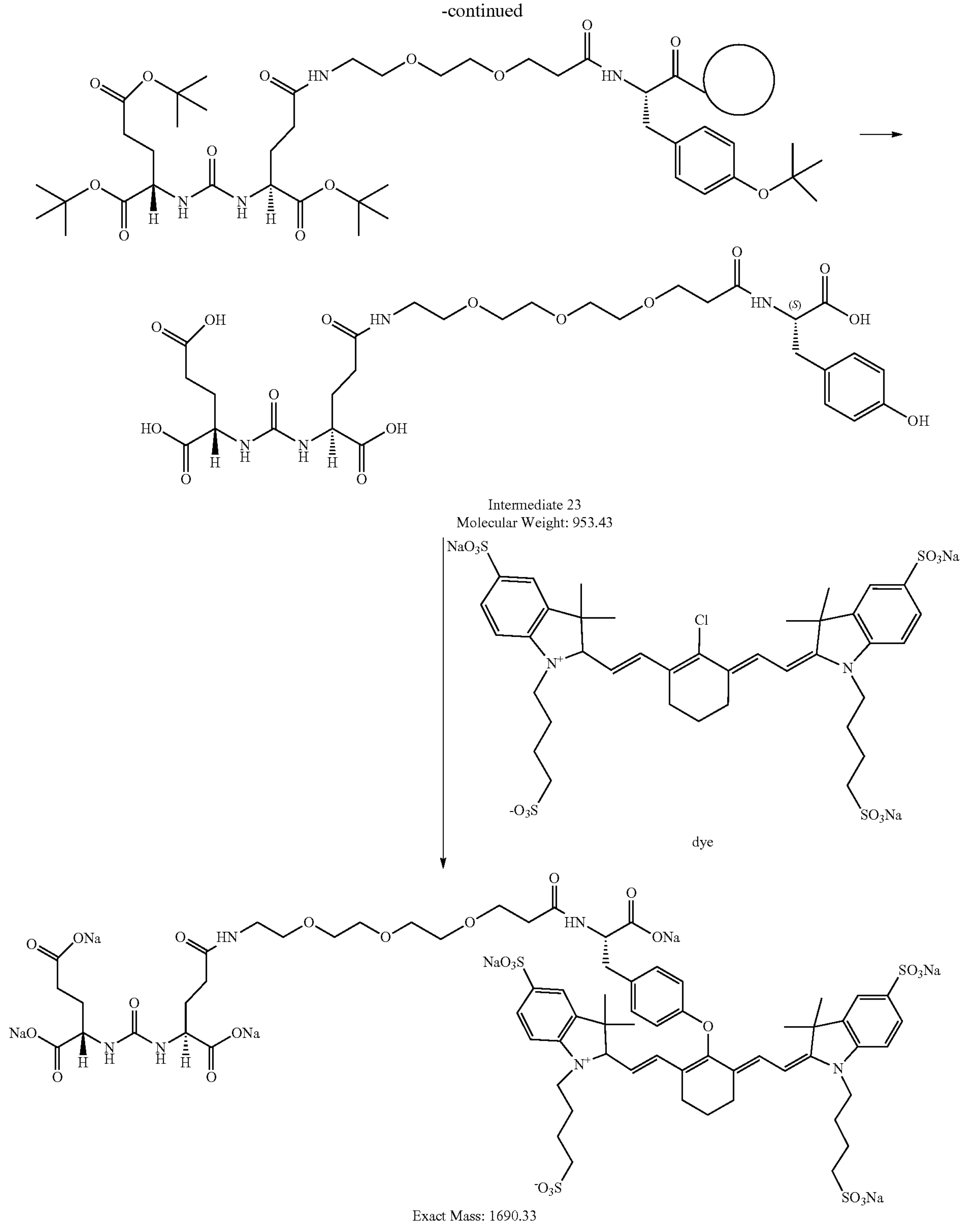

Intermediate 23
Molecular Weight: 953.43 dye

Exact Mass: 1690.33

The intermediate 1 (200 mg) obtained from the solid-phase synthesis was placed in a three-necked flask. 3.0 eq (in this example, eq refers to the molar multiple of CTC resin, the same below) of Fmoc-NH-PEG$_3$-$CH_2CH_2COOH$ was dissolved in 12 mL of DMF, then 3.0 eq of HOBt and 3.8 eq of DIC were added and activated for 6 min. The reaction was carried out under a nitrogen atmosphere for 1 h. The resin was washed with DMF 4 times. Subsequently, the N-terminal Fmoc protecting group was removed using 20% piperidine/DMF solution to make the N-terminal a free amino group, and the resin was washed with DMF 5 times to obtain intermediate 22;

3.0 eq of 3-BOC-DUPA were dissolved in 7V of DMF relative to the resin, then 3.0 eq of HBTU, 1.5 eq of HOBt, and 4.5 eq of DIEA were added and activated for 5 min. The mixture was added to intermediate 22 and the reaction was carried out under a nitrogen atmosphere for 1 h. The resin was washed with DMF 5 times;

Methanol was Added for Concentration, and the Product was Dried.

The target polypeptide was cleaved from the resin and the side-chain protecting groups were removed using a cleavage solution (trifluoroacetic acid:$H_2O$:triisopropylsilane=90:5:5, v/v) (reacted at 25° C. for 3 h). The mixture was subjected to suction filtration. The filtrate was added to methyl tert-butyl ether, and a precipitate was precipitated. The suspension was centrifuged to obtain a crude product of peptide-linked DUPA, which was subjected to preparative separation and lyophilized to obtain intermediate 23.

Condensation of Intermediate 23 and Dye: 50 mg of intermediate 23 and the dye were placed in a 25 mL single-necked flask at a molar ratio of 1:1. Purified water (40V relative to the resin) was used to dissolve 6 eq of $Na_2CO_3$. The mixture was added to the reaction flask and stirred at 70° C. for 1 h. The reaction mixture was subjected to preparative purification to obtain 23 mg of the product.

LCMS: $[M-7Na+4H]^{3+}$=511.2, molecular weight of target compound sodium salt: 1690.33.

$^1$H NMR (400 MHz, D2O): δ 7.92 (s, 2H), 7.79 (s, 4H), 7.43-7.22 (m, 4H), 7.19-7.02 (m, 2H), 6.29-6.09 (m, 1H), 4.52-4.33 (m, 1H), 4.23-3.97 (m, 6H), 3.64-3.14 (m, 17H), 3.04-2.56 (m, 9H), 2.48-2.33 (m, 4H), 2.33-2.23 (m, 2H), 2.19-1.99 (m, 2H), 1.99-1.70 (m, 12H), 1.43-1.30 (m, 12H).

The target compound was detected using the experimental method demonstrated in Example 11: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications—indicating more sensitivity during surgery; and rapid clearance—indicating faster clearance post-surgery and superior safety advantages.

Example 31

The target compound prepared in this example was:

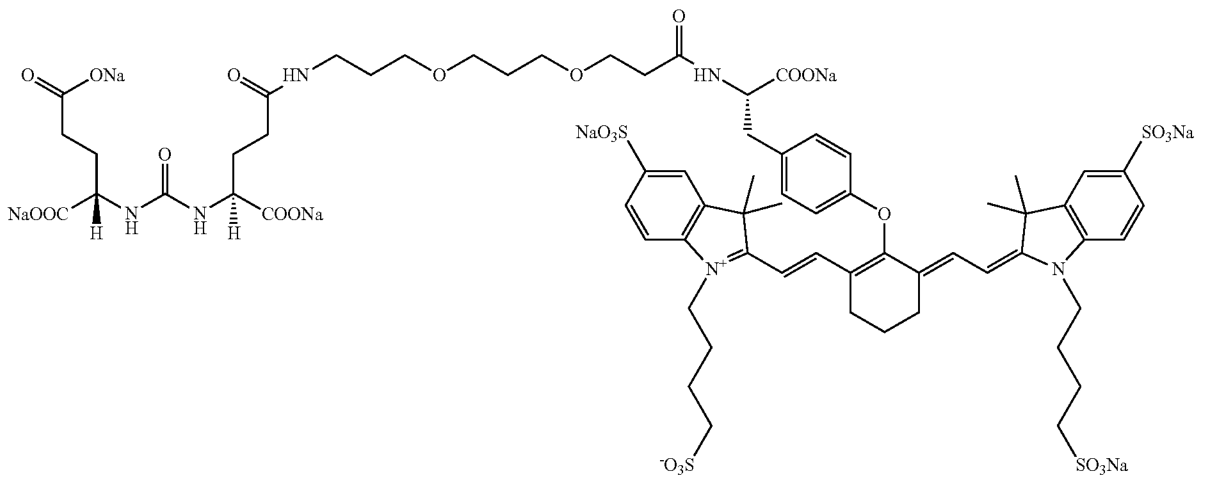

The preparation procedure was as follows:

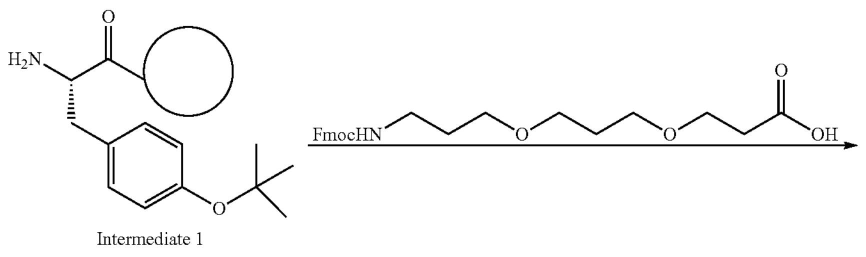

Intermediate 1

-continued
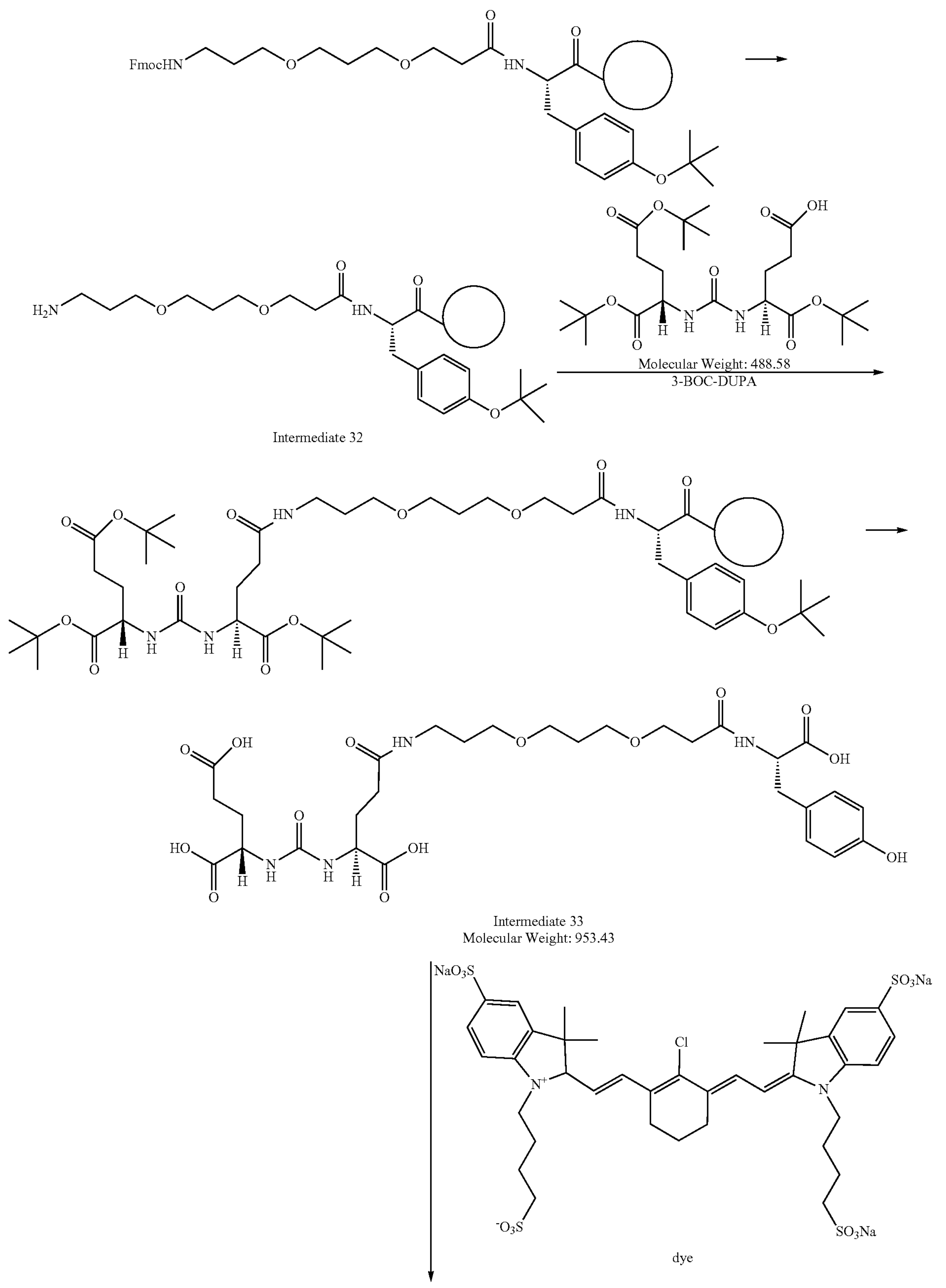
Intermediate 32
Intermediate 33
Molecular Weight: 953.43
dye -continued

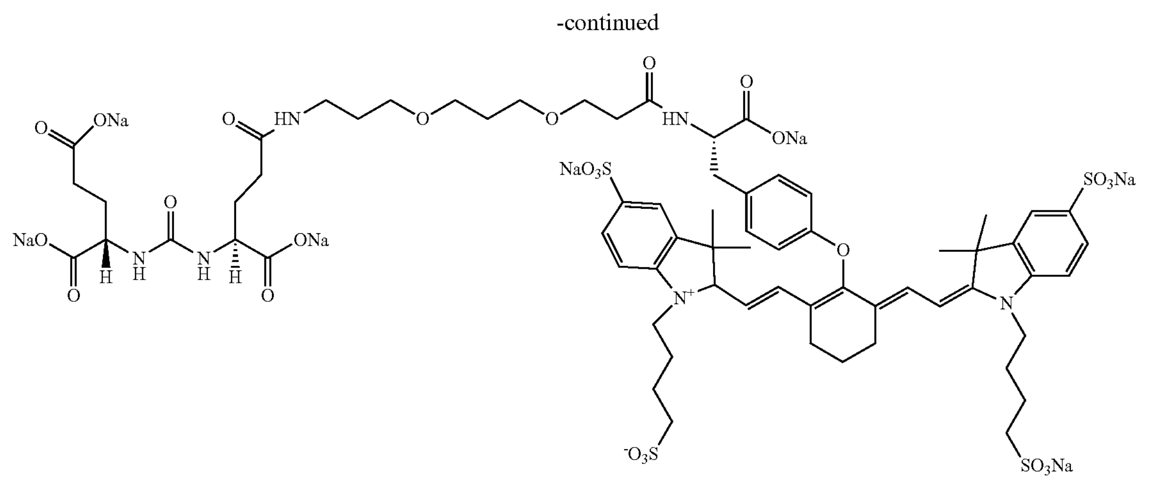

Exact Mass: 1647.34

The intermediate 1 obtained from the solid-phase synthesis was placed in a three-necked flask. 3.0 eq (in this example, eq refers to the molar multiple of CTC resin, the same below) of Fmoc-NH—$(CH_2CH_2CH_2O)_2$—$CH_2CH_2COOH$ was dissolved in 7V of DMF relative to the resin, then 3.0 eq of HOBt and 3.8 eq of DIC were added and activated for 6 min. The reaction was carried out under a nitrogen atmosphere for 1 h. The resin was washed with DMF 4 times. Subsequently, the N-terminal Fmoc protecting group was removed using 20% piperidine/DMF solution to make the N-terminal a free amino group, and the resin was washed with DMF 5 times to obtain intermediate 32;

3.0 eq of 3-BOC-DUPA were dissolved in 7V of DMF relative to the resin, then 3.0 eq of HBTU, 1.5 eq of HOBt, and 4.5 eq of DIEA were added and activated for 5 min. The mixture was added to intermediate 32 and the reaction was carried out under a nitrogen atmosphere for 1 h. The resin was washed with DMF 5 times;

Methanol was added for concentration, and the product was dried.

The target polypeptide was cleaved from the resin and the side-chain protecting groups were removed using a cleavage solution (trifluoroacetic acid:$H_2O$:triisopropylsilane=90:5:5, v/v) (reacted at 30° C. for 3 h). The mixture was subjected to suction filtration. The filtrate was added to methyl tert-butyl ether, and a precipitate was precipitated. The suspension was centrifuged to obtain a crude product of peptide-linked DUPA, which was subjected to preparative separation and lyophilized to obtain intermediate 33.

Condensation of Intermediate 33 and Dye: 50 mg of intermediate 33 and the dye were placed in a 25 mL single-necked flask at a molar ratio of 1:1. Purified water (40V relative to the resin) was used to dissolve 6 eq of $Na_2CO_3$. The mixture was added to the reaction flask and stirred at 70° C. for 1 h. The reaction mixture was subjected to preparative purification to obtain 35 mg.

LCMS: $[M-7Na+4H]^{3+}$=505.6, molecular weight of target compound sodium salt: 1674.34.

$^1H$ NMR (400 MHz, D2O): δ 7.92 (s, 2H), 7.79 (s, 4H), 7.43-7.22 (m, 4H), 7.19-7.02 (m, 2H), 6.29-6.09 (m, 1H), 4.52-4.33 (m, 1H), 4.23-3.97 (m, 6H), 3.64-3.14 (m, 17H), 3.04-2.56 (m, 9H), 2.48-2.33 (m, 4H), 2.33-2.23 (m, 2H), 2.19-1.99 (m, 2H), 1.99-1.70 (m, 16H), 1.43-1.30 (m, 12H).

The target compound was detected using the experimental method demonstrated in Example 11: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications-indicating more sensitivity during surgery; and rapid clearance-indicating faster clearance post-surgery and superior safety advantages.

Example 41
The target compound prepared in this example was:
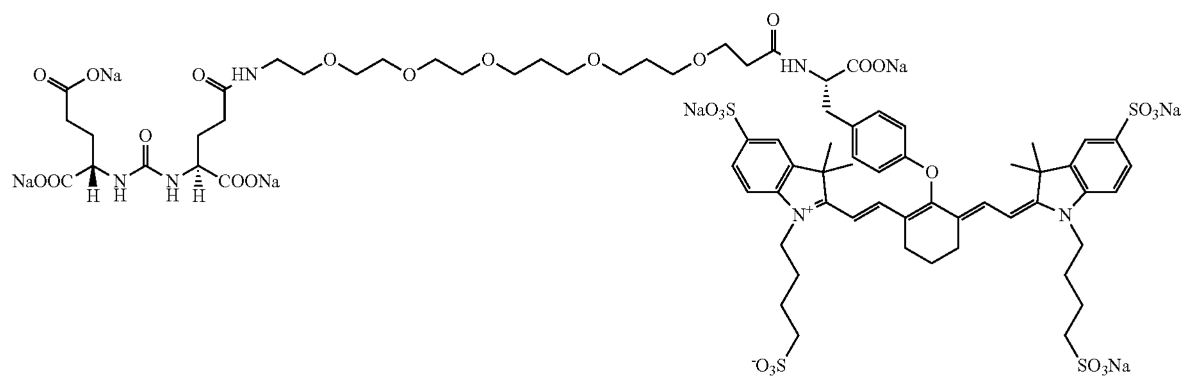
The preparation procedure was as follows:

Intermediate 1

Molecular Weight: 488.58
3-BOC-DUPA

Intermediate 42

-continued
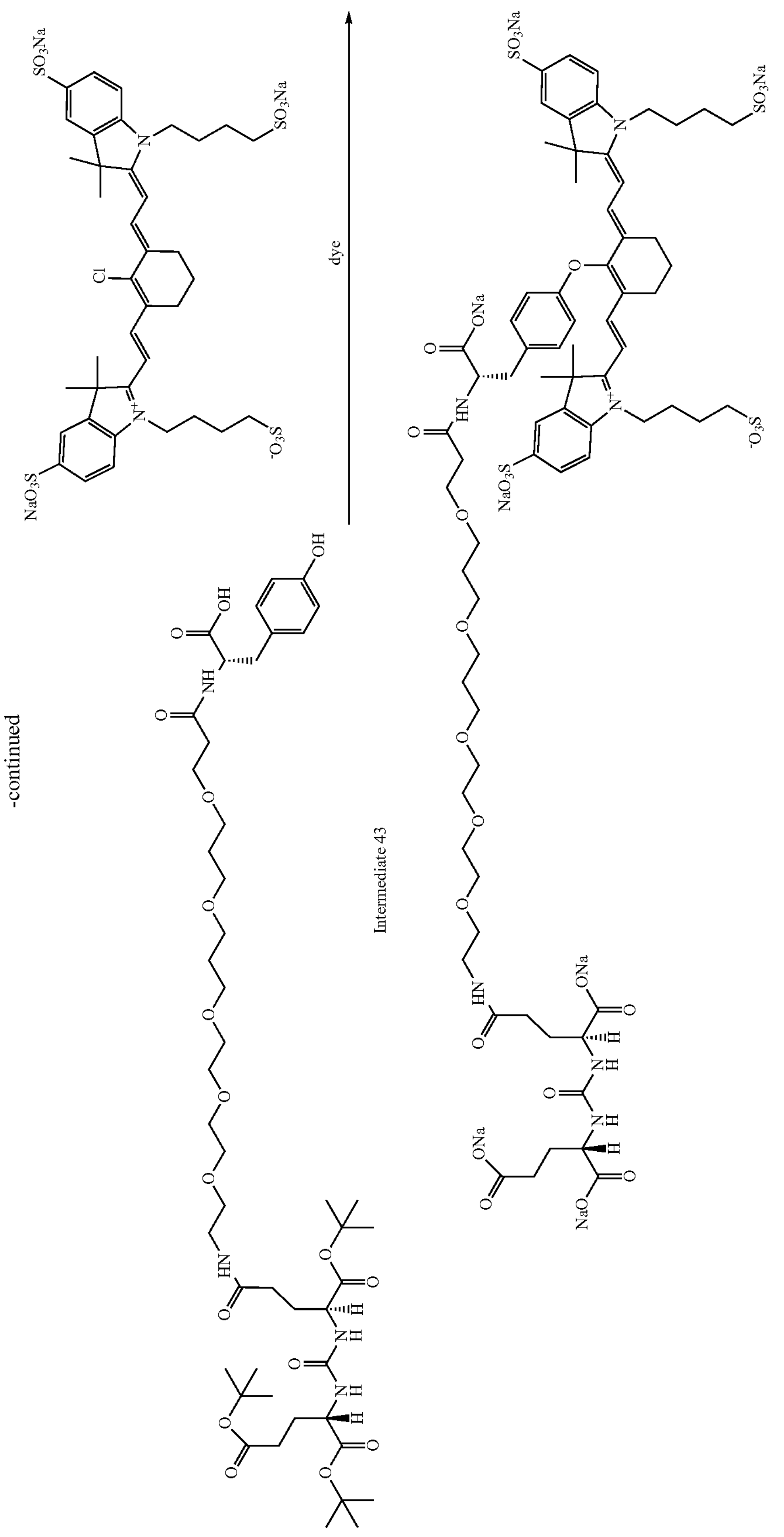
Intermediate 43
Exact Mass: 1806.42

-continued
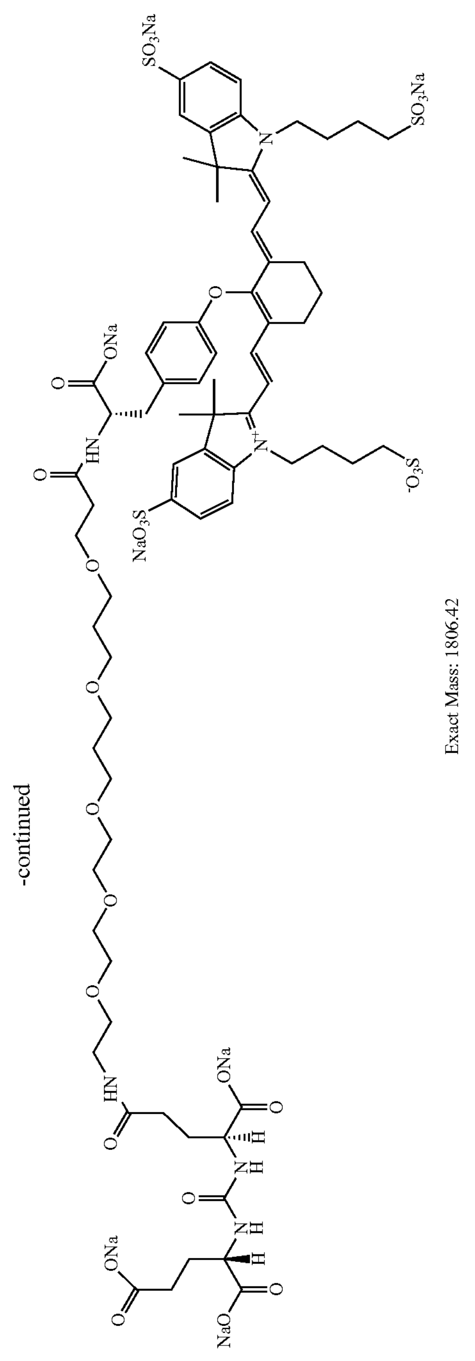
Exact Mass: 1806.42

The intermediate 1 (240 mg) obtained from the solid-phase synthesis was placed in a three-necked flask. 3.0 eq (in this example, eq refers to the molar multiple of CTC resin, the same below) of Fmoc-NH-PEG$_3$-$(CH_2CH_2CH_2O)_2$—$CH_2CH_2COOH$ was dissolved in 12 mL of DMF, then 3.0 eq of HOBt and 3.8 eq of DIC were added and activated for 6 min. The reaction was carried out under a nitrogen atmosphere for 1 h. The resin was washed with DMF 4 times. Subsequently, the N-terminal Fmoc protecting group was removed using 20% piperidine/DMF solution to make the N-terminal a free amino group, and the resin was washed with DMF 5 times to obtain intermediate 42;

3.0 eq of 3-BOC-DUPA were dissolved in 7V of DMF relative to the resin, then 3.0 eq of HBTU, 1.5 eq of HOBt, and 4.5 eq of DIEA were added and activated for 5 min. The mixture was added to intermediate 42 and the reaction was carried out under a nitrogen atmosphere for 1 h. The resin was washed with DMF 5 times;

Methanol was added for concentration, and the product was dried.

The target polypeptide was cleaved from the resin and the side-chain protecting groups were removed using a cleavage solution (trifluoroacetic acid:$H_2O$:triisopropylsilane=90:5:5, v/v) (reacted at 20° C. for 4 h). The mixture was subjected to suction filtration. The filtrate was added to methyl tert-butyl ether, and a precipitate was precipitated. The suspension was centrifuged to obtain a crude product of peptide-linked DUPA, which was subjected to preparative separation and lyophilized to obtain intermediate 43.

Condensation of Intermediate 43 and Dye: 50 mg of intermediate 43 and the dye were placed in a 25 mL single-necked flask at a molar ratio of 1:1. Purified water (40V relative to the resin) was used to dissolve 6 eq of $Na_2CO_3$. The mixture was added to the reaction flask and stirred at 70° C. for 1 h. The reaction mixture was subjected to preparative purification to obtain 27 mg of the product.

LCMS: $[M-7Na+4H]^{3+}$=549.6, molecular weight of target compound sodium salt: 1806.42.

$^1H$ NMR (400 MHz, D2O): δ 7.92 (s, 2H), 7.79 (s, 4H), 7.43-7.22 (m, 4H), 7.19-7.02 (m, 2H), 6.29-6.09 (m, 1H), 4.52-4.33 (m, 1H), 4.23-3.97 (m, 6H), 3.64-3.14 (m, 29H), 3.04-2.56 (m, 9H), 2.48-2.33 (m, 4H), 2.33-2.23 (m, 2H), 2.19-1.99 (m, 2H), 1.99-1.70 (m, 16H), 1.43-1.30 (m, 12H).

The target compound was detected using the experimental method demonstrated in Example 1: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications-indicating more sensitivity during surgery; and rapid clearance-indicating faster clearance post-surgery and superior safety advantages.

Example 51

The target compound prepared in this example was:

The preparation procedure was as follows:

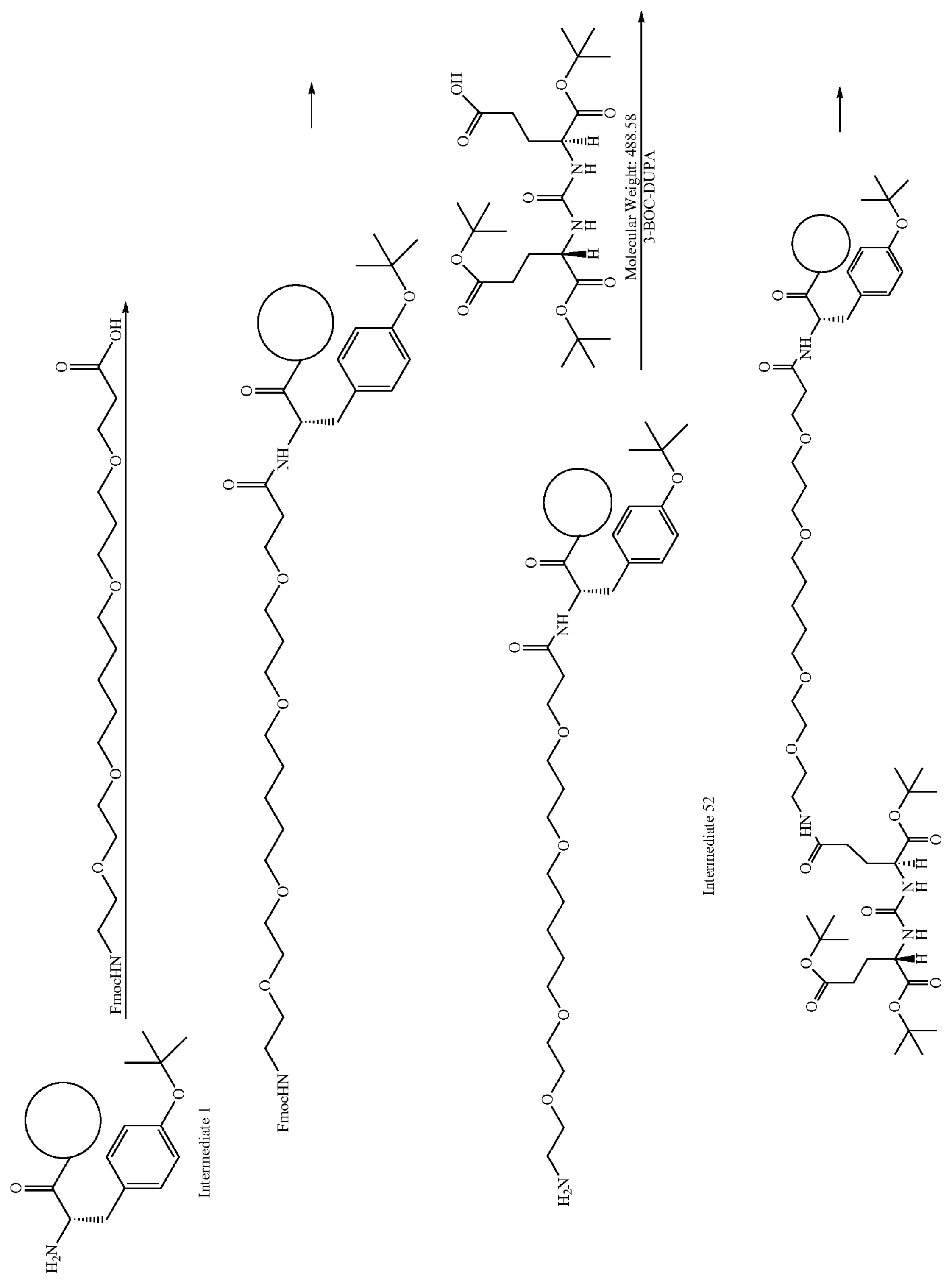
Intermediate 1
Molecular Weight: 488.58
3-BOC-DUPA
Intermediate 52

-continued
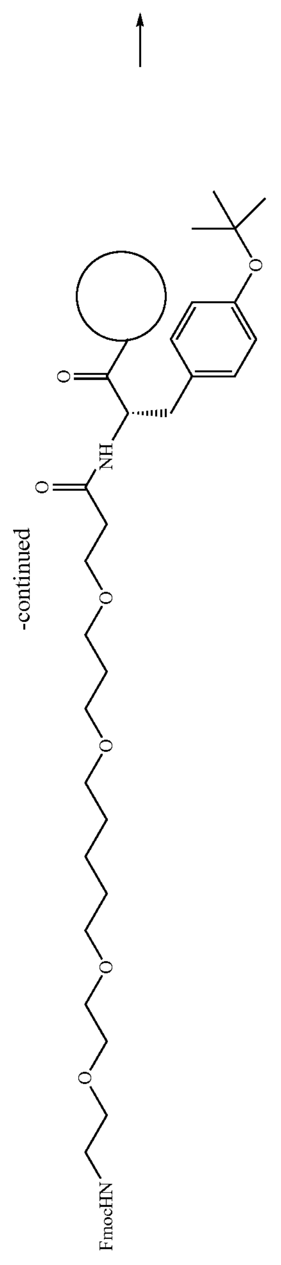

-continued
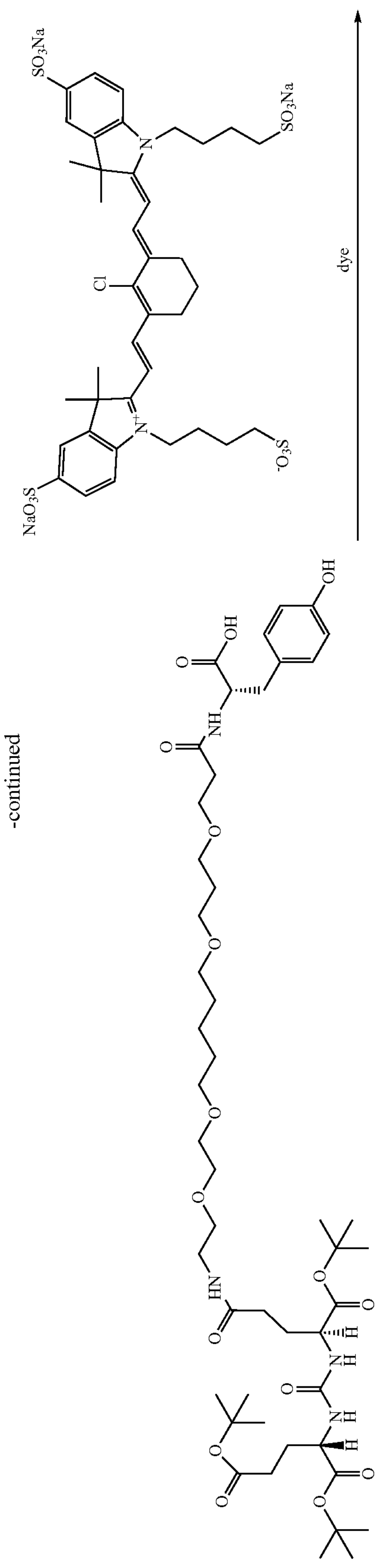
Intermediate 53
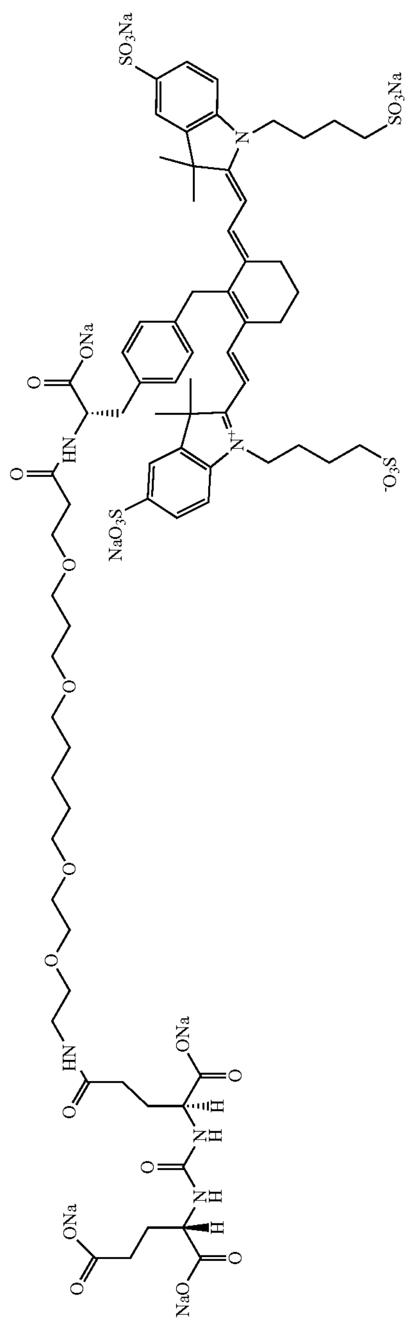
Exact Mass: 1790.42

-continued

Exact Mass: 1790.42

The intermediate 1 (200 mg) obtained from the solid-phase synthesis was placed in a three-necked flask. 3.0 eq (in this example, eq refers to the molar multiple of CTC resin, the same below) of Fmoc-NH-$PEG_2$-$(CH_2)_5$O—$(CH_2)_3$O—$CH_2CH_2COOH$ was dissolved in 7V of DMF relative to the resin, then 3.0 eq of HOBt and 3.8 eq of DIC were added and activated for 6 min. The reaction was carried out under a nitrogen atmosphere for 1 h. The resin was washed with DMF 4 times. Subsequently, the N-terminal Fmoc protecting group was removed using 20% piperidine/DMF solution to make the N-terminal a free amino group, and the resin was washed with DMF 5 times to obtain intermediate 52;

3.0 eq of 3-BOC-DUPA were dissolved in 7V of DMF relative to the resin, then 3.0 eq of HBTU, 1.5 eq of HOBt, and 4.5 eq of DIEA were added and activated for 5 min. The mixture was added to intermediate 52 and the reaction was carried out under a nitrogen atmosphere for 1 h. The resin was washed with DMF 5 times;

Methanol was added for concentration, and the product was dried.

The target polypeptide was cleaved from the resin and the side-chain protecting groups were removed using a cleavage solution (trifluoroacetic acid:$H_2O$:triisopropylsilane=90:5:5, v/v) (reacted at 30° C. for 3 h). The mixture was subjected to suction filtration. The filtrate was added to methyl tert-butyl ether, and a precipitate was precipitated. The suspension was centrifuged to obtain a crude product of peptide-linked DUPA, which was subjected to preparative separation and lyophilized to obtain intermediate 53.

Condensation of Intermediate 53 and Dye: 50 mg of intermediate 53 and the dye were placed in a 25 mL single-necked flask at a molar ratio of 1:1. Purified water (40V relative to the resin) was used to dissolve 7 eq of $Na_2CO_3$. The mixture was added to the reaction flask and stirred at 70° C. for 1 h. The reaction mixture was subjected to preparative purification to obtain 35 mg of the product.

LCMS: $[M-7Na+4H]^{3+}$=544.3, molecular weight of target compound sodium salt: 1790.42.

$^1$H NMR (400 MHz, D2O): δ 7.92 (s, 2H), 7.79 (s, 4H), 7.43-7.22 (m, 4H), 7.19-7.02 (m, 2H), 6.29-6.09 (m, 1H), 4.52-4.33 (m, 1H), 4.23-3.97 (m, 6H), 3.64-3.14 (m, 25H), 3.04-2.56 (m, 9H), 2.48-2.33 (m, 4H), 2.33-2.23 (m, 2H), 2.19-1.99 (m, 2H), 1.99-1.70 (m, 14H), 1.50-1.56 (m, 6H), 1.43-1.30 (m, 12H).

The target compound was detected using the experimental method demonstrated in Example 1: the negative cell line PC3 had no binding ability to PSMA receptor, the positive cell 22RV1 had a certain binding ability to PSMA receptor, and the target compound showed good affinity. The target compound could be enriched in the prostate cancer tumor site within a certain period of time. The target compound showed good targeting properties. In experiments using mice as experimental subjects, the compound of this example exhibited greater fluorescence values at the tumor site than OTL78; and a good TBR (tumor-to-background ratio) from about 2 h to 72 h. The compound of this example exhibited stronger discrimination capability (approximately 5-fold) and higher TBR. The higher TBR can make the tumor boundary line clearer during surgery and obtain more accurate resection margins. The compound of this example was cleared more rapidly in rats in vivo, thereby correspondingly increasing its safety factor. In the acute toxicity experiment on rats, no toxic reactions were observed in the three dose groups of high, medium, and low doses. These suggests that the compound in this example exhibits a high signal-to-noise ratio in fluorescence imaging applications—indicating more sensitivity during surgery; and rapid clearance—indicating faster clearance post-surgery and superior safety advantages.

All aspects, examples, features, and embodiments of the present disclosure are to be regarded as illustrative in all respects and are not intended to limit the scope of the present disclosure, which is defined solely by the appended claims. Other examples, modifications, and uses will be apparent to those skilled in the art without departing from the spirit and scope of the claimed disclosure.

In addition, the inventors of the present application conducted experiments with other raw materials, process operations, and process conditions described in this specification, following the aforementioned examples, and all yielded relatively ideal results.

Although the present disclosure has been described with reference to illustrative examples, it will be understood by those skilled in the art that various other changes, omissions, and/or additions may be made without departing from the spirit and scope of the present disclosure, and that elements of the examples may be substituted with substantially equivalents. Furthermore, numerous modifications may be made without departing from the scope of the present disclosure to adapt specific situations or materials to the teachings of the present disclosure. Therefore, it is not intended herein that the present disclosure be limited to the specific examples disclosed for carrying out the present disclosure, but rather that the present disclosure encompass all examples falling within the scope of the appended claims. In addition, unless specifically stated, any use of the terms first, second, etc., does not denote any order or importance, but rather the terms first, second, etc., are used to distinguish one element from another.

The invention claimed is:

1. A compound having a structural formula as follows:

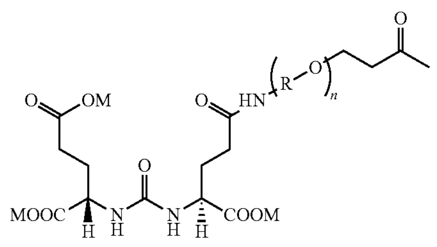

-continued

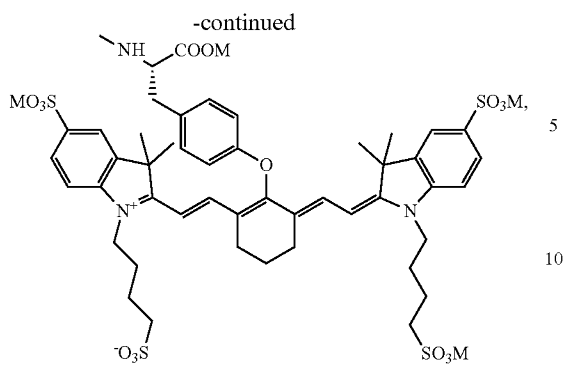

wherein cation M is selected from alkali metal cations, R is C2-C5 alkylene, and n is an integer in the range of 2-5.

2. The compound according to claim 1, wherein the cation M is selected from $Na^+$, $K^+$, and $Li^+$.

3. A preparation method for the compound according to claim 1, comprising the following steps:

preparing intermediate A and intermediate B, wherein intermediate A is

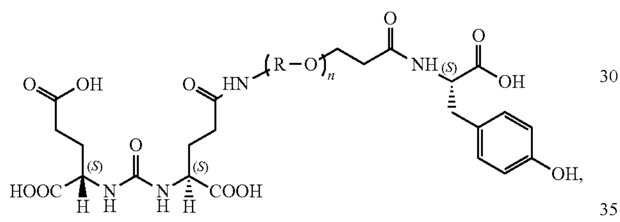

R is C2-C5 alkylene, and n is an integer in the range of 2-5; intermediate B is

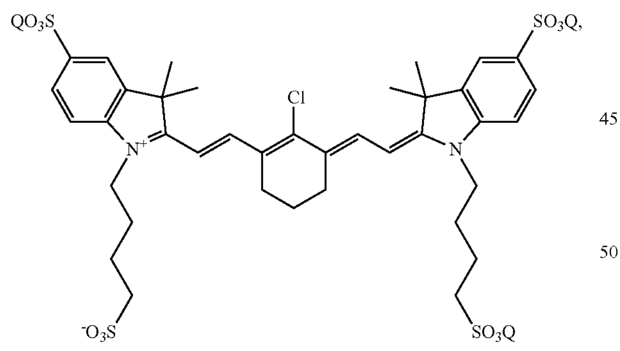

and the cation Q is selected from $Na^+$, $K^+$, and $Li^+$;

stirring and reacting intermediate A with intermediate B, and separating to obtain a target compound.

4. The preparation method for the compound according to claim 3, wherein the intermediate A is prepared by:

A1: preparing swollen CTC resin, reacting with Fmoc-Tyr(tBu)-OH/DIEA, and then deprotecting to obtain intermediate 1;

B1: reacting intermediate 1 with Fmoc-NH-$PEG_2$-$CH_2CH_2COOH$/HOBt after activation, and deprotecting to obtain intermediate 2;

C1: reacting intermediate 2 with compound 1/HBTU/HOBt after activation, contracting, cleaving, and deprotecting to obtain intermediate A, wherein compound 1 is

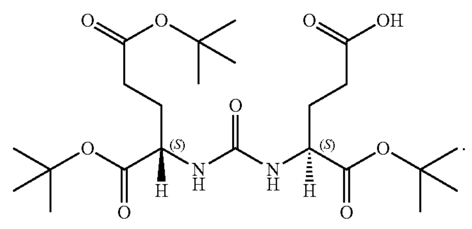

5. The preparation method for the compound according to claim 3, wherein the intermediate B is prepared by:

A2: reacting phosphorus trichloride with DMF and cyclohexanone, then mixing the resulting mixture with ice under stirring and reacting, separating a precipitate, and washing, purifying, and drying to obtain compound 2;

stirring and reacting 4-hydrazinobenzenesulfonic acid, sodium acetate, and 3-methyl-2-butanone in acetic acid under a protective gas atmosphere, then adding diethyl ether for precipitation, washing and drying to obtain compound 3; reacting the compound 3 with 1,4-butanesultone in o-dichlorobenzene under a protective gas atmosphere, then washing, separating, and drying to obtain compound 4;

B2: heating the compound 2, compound 4, and sodium acetate in methanol, then adding acetic anhydride to react, separating and purifying at room temperature to obtain intermediate B.

6. The preparation method for the compound according to claim 3, wherein the conditions for the stirring and reacting are stirring and reacting at 65-75° C. for 0.5-1.5 h.

7. A composition comprising the compound according to claim 1.

8. A kit comprising the compound according to claim 1.

9. A kit comprising the composition according to claim 7.

10. A flow cytometry detection reagent, comprising the compound according to claim 1.

11. A flow cytometry detection reagent, comprising the composition according to claim 7.

12. A fluorescent detection material, comprising the compound according to claim 1.

13. A fluorescent detection material, comprising the composition according to claim 7.

14. A fluorescent detection material, comprising the kit according to claim 8.

15. The compound according to claim 1, wherein R is C2 alkylene.

16. The compound according to claim 1, wherein n is 2.

17. The compound according to claim 1, wherein the cation M is $Na^+$.

18. A compound, which is selected from any one of the following compounds:
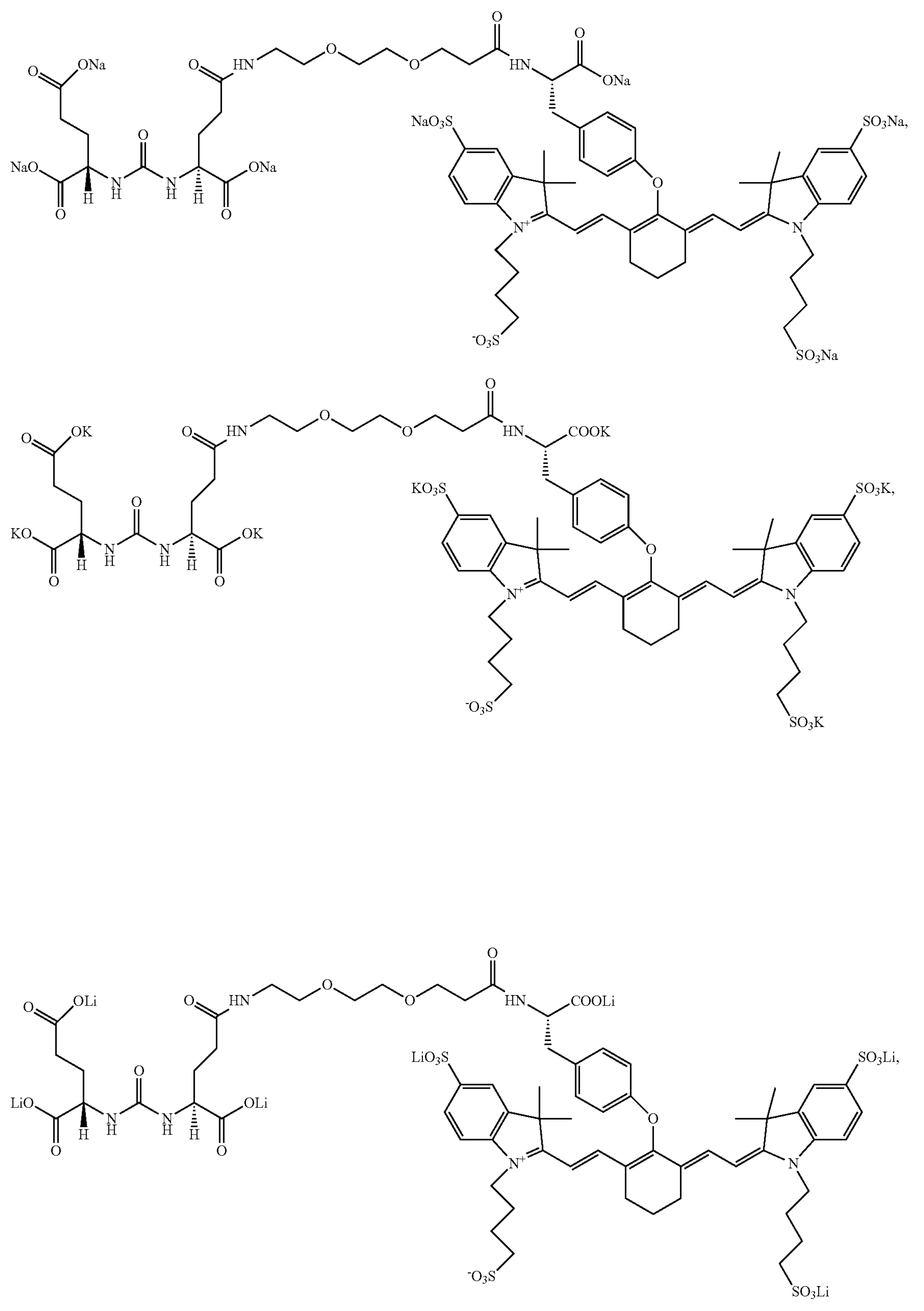

-continued
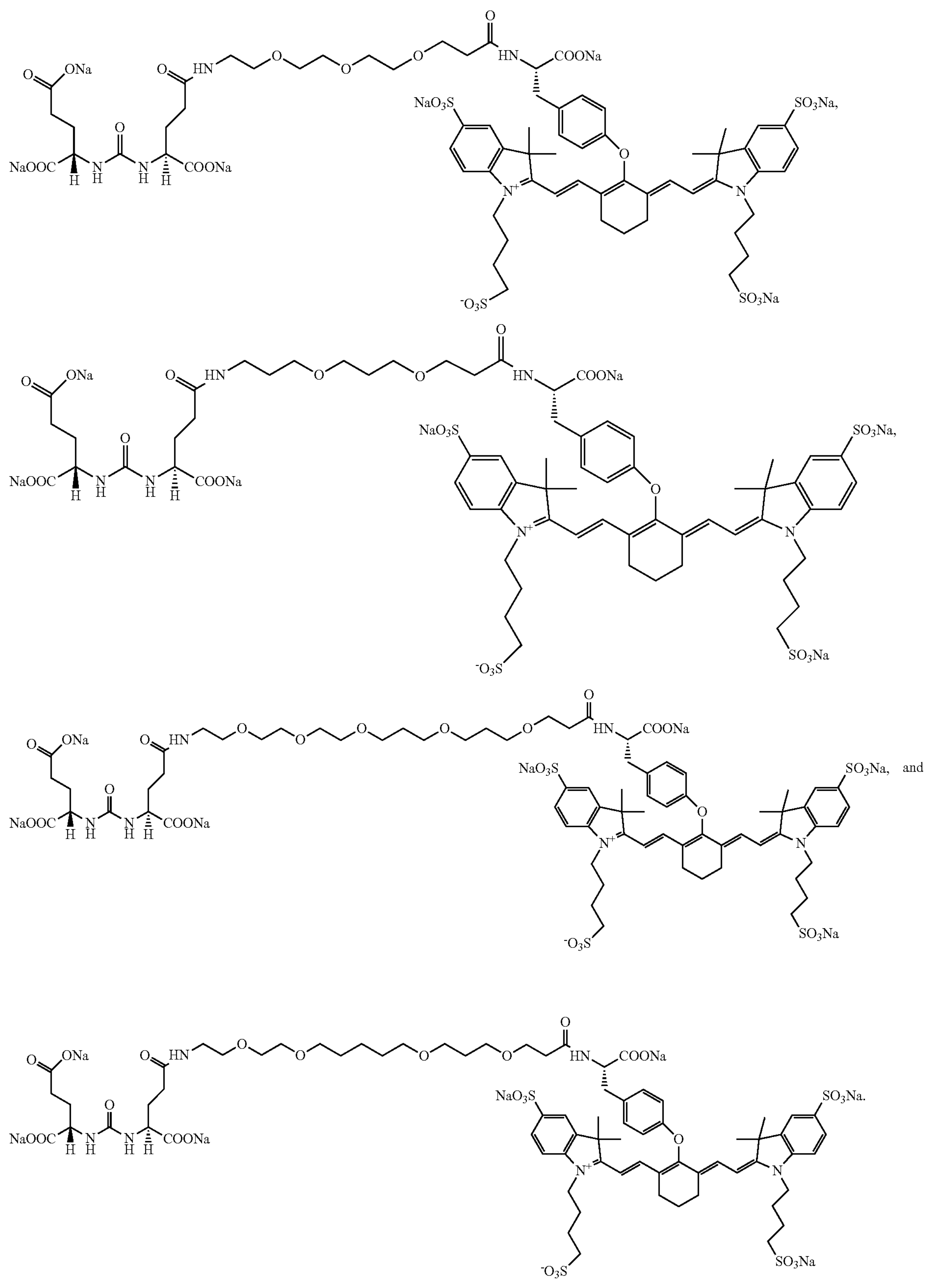
, , and .

19. The compound according to claim 18, which is the following compound:
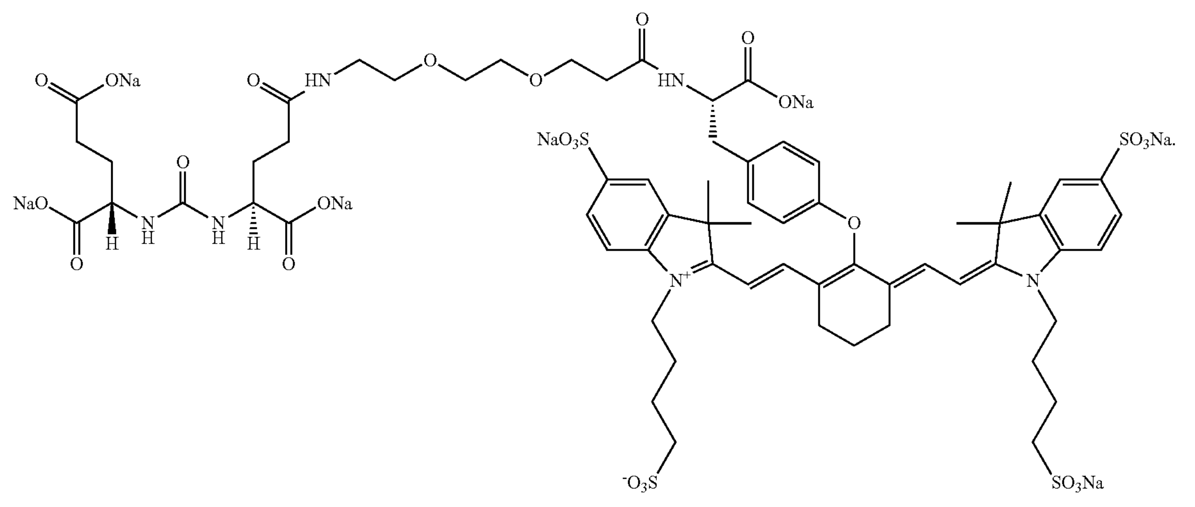
* * * * *